United States Patent
Hamilton et al.

(10) Patent No.: US 9,290,660 B2
(45) Date of Patent: Mar. 22, 2016

(54) METHOD AND APPARATUS FOR IDENTIFYING AND CHARACTERIZING MATERIAL SOLVENTS AND COMPOSITE MATRICES AND METHODS OF USING SAME

(71) Applicant: WISYS TECHNOLOGY FOUNDATION, Madison, WI (US)

(72) Inventors: James P. Hamilton, Platteville, WI (US); Philip V. Streich, Platteville, WI (US)

(73) Assignee: WISYS TECHNOLOGY FOUNDATION, INC., Madison, WI (US)

( * ) Notice: Subject to any disclaimer, the term of this patent is extended or adjusted under 35 U.S.C. 154(b) by 0 days.

(21) Appl. No.: 13/666,655

(22) Filed: Nov. 1, 2012

(65) Prior Publication Data

US 2013/0075650 A1    Mar. 28, 2013

Related U.S. Application Data

(62) Division of application No. 12/811,776, filed as application No. PCT/US2009/030306 on Jan. 7, 2009, now Pat. No. 9,109,113.

(60) Provisional application No. 61/201,055, filed on Dec.

(Continued)

(51) Int. Cl.
  *C08K 3/04* (2006.01)
  *C08L 79/04* (2006.01)

(Continued)

(52) U.S. Cl.
  CPC ............... *C08L 79/04* (2013.01); *B82Y 30/00* (2013.01); *B82Y 40/00* (2013.01); *C01B 31/0438* (2013.01); *C01B 31/0446* (2013.01);

(Continued)

(58) Field of Classification Search
  CPC ........................................................ C08K 3/04
  USPC ........................................................ 524/496
  See application file for complete search history.

(56) References Cited

U.S. PATENT DOCUMENTS 6,828,015 B2 * 12/2004 Hirata et al. ................... 428/323
7,566,410 B2 *  7/2009 Song et al. ..................... 252/511

(Continued)

FOREIGN PATENT DOCUMENTS

| JP | 2007169112 | 7/2007 |
| JP | 2008214140 | 9/2008 |
| WO | 2007047084 | 4/2007 |

OTHER PUBLICATIONS

Ausman et al. ("Organic Solvent Dispersions of Single-Walled Carbon Nanotubes: Toward Solutions of Pristine Nanotubes", J. Phys. Chem. B, Sep. 28, 2000, vol. 104, pp. 8911-8915).*

(Continued)

*Primary Examiner* — Bijan Ahvazi
*Assistant Examiner* — Lanee Reuther
(74) *Attorney, Agent, or Firm* — Boyle Fredrickson, S.C.

(57) ABSTRACT

Solvents for macromolecules generally believed to be insoluble in their pristine form are identified by generation of a "solvent resonance" in the relationship between solvent quality (deduced by Rayleigh scattering) and an intrinsic property of solvents. A local extreme of the solvent resonance identifies the ideal intrinsic property of an ideal solvent which may then be used to select a particular solvent or solvent combination. A solvent for graphene is used in the production of transparent conductive electrodes.

21 Claims, 18 Drawing Sheets

Related U.S. Application Data 5, 2008, provisional application No. 61/098,419, filed on Sep. 19, 2008, provisional application No. 61/051,758, filed on May 9, 2008, provisional application No. 61/019,428, filed on Jan. 7, 2008.

(51) Int. Cl.

| | |
|---|---|
| *C01B 31/04* | (2006.01) |
| *B82Y 30/00* | (2011.01) |
| *B82Y 40/00* | (2011.01) |
| *C03C 17/22* | (2006.01) |
| *C09D 1/00* | (2006.01) |
| *C09D 5/24* | (2006.01) |
| *C09D 7/00* | (2006.01) |
| *G01N 21/49* | (2006.01) |
| *H01B 1/04* | (2006.01) |
| *H01B 1/24* | (2006.01) |
| *C09D 179/04* | (2006.01) |
| *H01G 11/32* | (2013.01) |

(52) U.S. Cl.
CPC ............ *C01B 31/0469* (2013.01); *C03C 17/22* (2013.01); *C08K 3/04* (2013.01); *C09D 1/00* (2013.01); *C09D 5/24* (2013.01); *C09D 7/001* (2013.01); *C09D 179/04* (2013.01); *G01N 21/49* (2013.01); *H01B 1/04* (2013.01); *H01B 1/24* (2013.01); *H01G 11/32* (2013.01); *C01B 2204/02* (2013.01); *C01B 2204/04* (2013.01); *C03C 2217/282* (2013.01); *C03C 2218/116* (2013.01); *Y02E 60/13* (2013.01); *Y10S 977/734* (2013.01); *Y10S 977/842* (2013.01); *Y10T 428/26* (2015.01); *Y10T 428/261* (2015.01)

(56) References Cited

U.S. PATENT DOCUMENTS

| | | | |
|---|---|---|---|
| 7,914,844 B2* | 3/2011 | Stankovich et al. | ............ 427/58 |
| 2007/0092432 A1 | 4/2007 | Prud'Homme et al. | |
| 2007/0158618 A1* | 7/2007 | Song et al. | .................... 252/500 |
| 2007/0284557 A1 | 12/2007 | Gruner et al. | |

OTHER PUBLICATIONS

Scott Gilje, et al., "A chemical route to graphene for device applications," Nano Letters, published on Web on Oct. 18, 2007, vol. 7, No. 11 p. 3394-3398.

Chinese Patent Appln. No. 200980108034X; Apr. 9, 2014 Office Action and English Translation, 14 pages.

Korean Patent Appln. No. 10-2010-7017475 Office Action dated Jan. 20,2015 (6 Pages), and English Translation (6 pages).

Wang et al., "Transparent, Conductive Graphene Electrodes for Dye-Sensitized Solar Cells", Nano Letters 2008, vol. 8, No. 1, pp. 323-327.

Giordani et al., "Debundling of Single-Walled Nanotubes by Dilution: Observation of Large Populations of Individual Nanotubes in Amide Solvent Dispersions", J. Phys. Chem. B 2006, 110, 15708-15718.

Australian Patent Appln. No. 2014202467, Office Action dated Feb. 11, 2015 (7Pages).

Hasan T. et al ", "Stabilization and 'Debundling' of Single-Wall Carbon Nanotube Dispersions in N-Methyl-2pyrrolidone (NMP) by Polyvinylpyrrolidone (PVP)", Journal of Physcial Chemistry C (2007, 111(34), p. 12594-12602.

Pellizzeri, S. et al., "Physical and electronic interactions between a straight chain conjugated polymer and single wall carbon nanotubes, in solution", Abstracts of Papers, 231st ACS National Meeting, Atlanta, GA, Mar. 26-30, 2006, CHED-312 Publisher; American Chemical Society, Washington, D.C.

Bryning, M.B. et al., "Thermal conductivity and interfacial resistance in single-wall carbon nanotube epoxy composites". Applied Physics Letters (2005), 87, 161909.

Fraczek, A. et al., "Dispersion of carbon nanotbues in a PAN-based composite matrix", Karbo (2007), 52(4), p. 201-206.

* cited by examiner

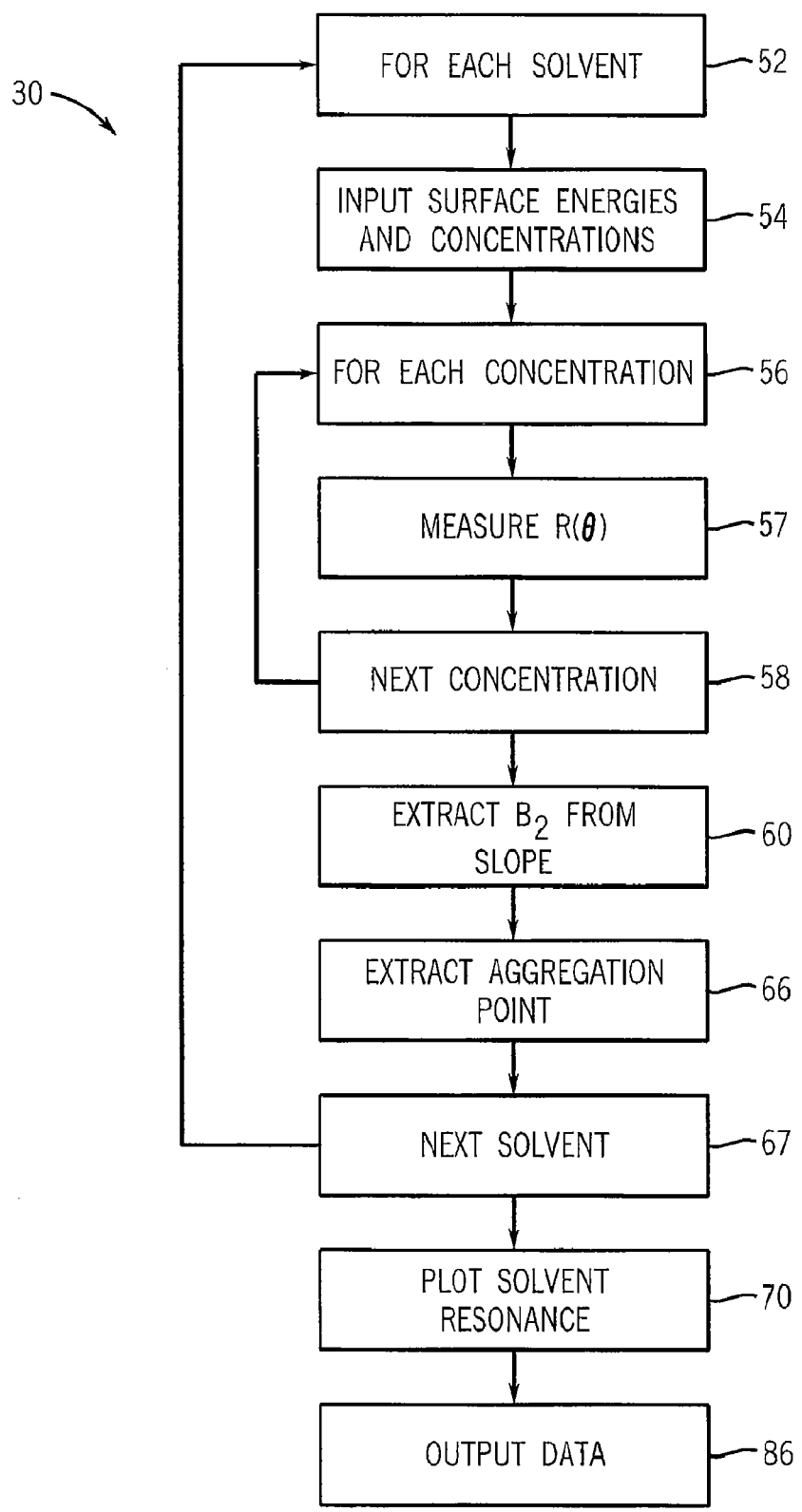

METHOD AND APPARATUS FOR IDENTIFYING AND CHARACTERIZING MATERIAL SOLVENTS AND COMPOSITE MATRICES AND METHODS OF USING SAME

CROSS-REFERENCE TO RELATED APPLICATIONS

This application claims priority as a divisional application from U.S. Non-Provisional patent application Ser. No. 12/811,776, filed on Jul. 6, 2010, which is a national stage filing under 35 USC 371 of International Application No. PCT/US2009/030306, filed Jan. 7, 2009, which claims priority from each of U.S. Provisional Patent Application Ser. No. 61/019,428, filed on Jan. 7, 2008; U.S. Provisional Patent Application Ser. No. 61/051,758, filed on May 9, 2008; U.S. Provisional Patent Application Ser. No. 61/098,419, filed on Sep. 19, 2008; and U.S. Provisional Patent Application Ser. No. 61/201,055, filed on Dec. 5, 2008, all of which are expressly incorporated by reference herein in their entirety.

STATEMENT REGARDING FEDERALLY SPONSORED RESEARCH OR DEVELOPMENT

N/A

BACKGROUND OF THE INVENTION

The present invention relates to a method and apparatus for identifying and characterizing optimum solvents for macromolecule and nanoparticle solutes, including, for example, solutes of carbon nanotubes or graphene as well as methods of using these solvents for the manufacture of articles and materials.

There is considerable interest in finding effective solvents for certain types of macromolecules. Such solvents could be used to promote the uniform dispersion of the macromolecules, for example, separating carbon nanotubes that tend to clump in "bundles", "ropes", or aggregations. A more uniform dispersion of macromolecules can improve composite materials or surface coatings that use those macromolecules. An effective solvent could also be used to exfoliate macromolecules from a mass, for example, to remove individual graphene sheets from bulk graphite. An effective solvent could be used for separation of macromolecules, for example, fractional precipitation of macromolecules of different molecular weights. A true solution, enabled by an effective solvent, can provide a delivery vehicle for the macromolecules that preserves suspension of the macromolecules as well as permits various novel manufacturing techniques.

Effective solvents for many valuable macromolecules are unknown. For example, pristine single wall carbon nanotubes (SWCNT or SWNT), like most carbon allotropes, are widely believed to be insoluble in organic or aqueous solvents. Pristine means, herein, not functionalized or chemically reacted with other elements such as oxygen. Solvent-based dispersal of SWNT currently relies on adding materials to the SWNT, for example, by covalent functionalization of the SWNT or by the addition of surfactants and/or dispersants to the surface of the SWNT. Some liquids are often loosely characterized as "solvents" without specifying the state of the solute. Some solutions are colloids or dispersions. In this respect, the literature sometimes discusses carbon nanotubes suspended in a solvent, however, it is understood to those of skill in this art that these are not thermodynamically stable solute/solvent systems in which significant concentrations of the macromolecules would be suspended indefinitely.

There are a number of techniques currently used to identify solvents for a given solute including solubility parameters and surface energies. The Hansen Solubility Parameters predict the effectiveness of a solvent by examining bond energies being an intrinsic property of the solvent and solute. When corresponding bond energies of the solvent and solute are close to each other, effective solvent action is predicted. The Hildebrand Solubility Parameter is a function of "cohesive energy density", a property intrinsic to a material and that measures an amount of energy needed to fully separate the molecules of the material. Again, solvents with a Hildebrand parameter close to the Hildebrand parameter of the target solute are expected to be effective solvents for the solute.

Both of these techniques for predicting the effectiveness of a solvent have an advantage of relying solely on intrinsic properties of the materials of the solvent and solute. For this reason, they can be implemented with a simple search of published literature for the intrinsic properties for the solvent and solute, each measured independently.

Nevertheless, these techniques have shortcomings, including, for example, the difficulty of accurately measuring the Hansen parameters and the failure of the techniques to account for some solubility influencing parameters such as molecular shape and size.

Normally, each of these techniques would be supplemented with an empirical measurement of an actual solution of the solvent and solute to determine the concentration of the solute at saturation. Such empirical measurements can be difficult to make with macromolecules that can enter into colloid-like suspensions that obscure the determination of solubility.

BRIEF SUMMARY OF THE INVENTION

The present inventors have developed an instrument that can identify solvent properties for a given solute. In using this instrument they have discovered that, in fact, true solvents exist for a number of macromolecules previously thought to be insoluble in their pristine state. These macromolecules include carbon nanotubes, graphene, and cellulose nanocrystals (nanocellulose). The invention is not limited to these few however and is expected to include boron nitride nanotubes as well as molybdenum sulfide and other lamellar materials like graphite and other nanotube materials. It is believed that a previously unrecognized general principle of nanomaterials has been uncovered by this invention and that many insoluble materials can be "solubilized". This discovery, has in, turn lead to the development of a number of thermodynamically stable liquid, solid or gel matrix materials incorporating these macromolecules. With respect to graphene, the inventors have discovered that the solvent can be used to generate thin transparent conductive layers and electrically contiguous graphene sheets.

Solvent Characterizing Instrument

The present invention provides a method and apparatus for identifying effective solvents by making empirical measurements of a "solvent quality" for a variety of solutions with different test solvents, each test solvent having a predetermined intrinsic property, for example, a known surface tension or surface energy. The present inventors have identified the existence of a "solvent resonance" in these measurements whose local extreme appears to accurately identify the intrinsic property of an ideal solvent (for a given solute). The intrinsic property identified by the solvent resonance can be employed to inform a search for a solvent having the best match to this intrinsic property. Similarly, the present inventors have identified the existence of a "material resonance" in these measurements whose local extreme appears to accurately identify the intrinsic property of an ideal matrix (for a given solute). The intrinsic property identified by the solute resonance can be employed to inform a search for a matrix having the best match to this intrinsic property and hence maximum composite strength or other material property via optimum (not necessarily maximum) solute/matrix interaction.

Macromolecules Solvents—Carbon Nanotubes

Using the above instrument, the present inventors have determined the properties of high-quality solvents for carbon nanotubes, both multi-wall and single wall. Such solvents are characterized by a chi value of less than −0.08, and may have a surface tension value between about 37 mJ/m$^2$ and about 40 mJ/m$^2$. Example solvents include: N-alkyl pyrrolidones such as CHP, NEP, NMP, N8P, and mixtures thereof. Polymers may be evaluated according to these solvent characteristics to create stable polymer matrices with highly dispersed carbon nanotubes. Functionalized nanotubes such as ODA (octyl decanoic acid) functionalized tubes have a different surface energy and a different optimum solvent blend or polymer matrix. For example, ODA functionalized nanotubes have an optimum solvent/matrix Hildebrand Parameter of between 18-21 MPa$^{1/2}$ and an optimum of about 19.5 MPa$^{1/2}$.

Macromolecules Solvents—Graphene

Using the above instrument, the present inventors have also determined the properties of high-quality solvents for graphene permitting it to be extracted from graphite. Such solvents are characterized by a chi value of less than 0.01, and may have a surface tension value between about 38.4 mJ/m$^2$ and about 40.4 mJ/m$^2$. Example solvents include: CHP, NMP and mixtures thereof. Again, polymers may be evaluated according to these solvent characteristics to create stable polymer matrices with highly dispersed graphene.

Solvent—Enabled Graphene Products

The discovery of a solvent for graphene has enabled a number of novel manufacturing processes and products. A transparent graphene electrode may be created by depositing solventized graphene on a substrate. Thus the present invention permits the development of a material having a conductive graphene coating. The present inventors have also determined that graphene sheets may self assemble at a liquid interface raising the potential to produce a continuous graphene sheet many square millimeters in area.

BRIEF DESCRIPTION OF THE DRAWINGS

FIG. 2 is a flow chart of a program executed by the computer system of FIG. 1 for characterizing optimal solvents for a given solute and for identifying the saturation point of given solutions;

DETAILED DESCRIPTION OF THE INVENTION

A. Instrument and Method of Use

Figure 1:
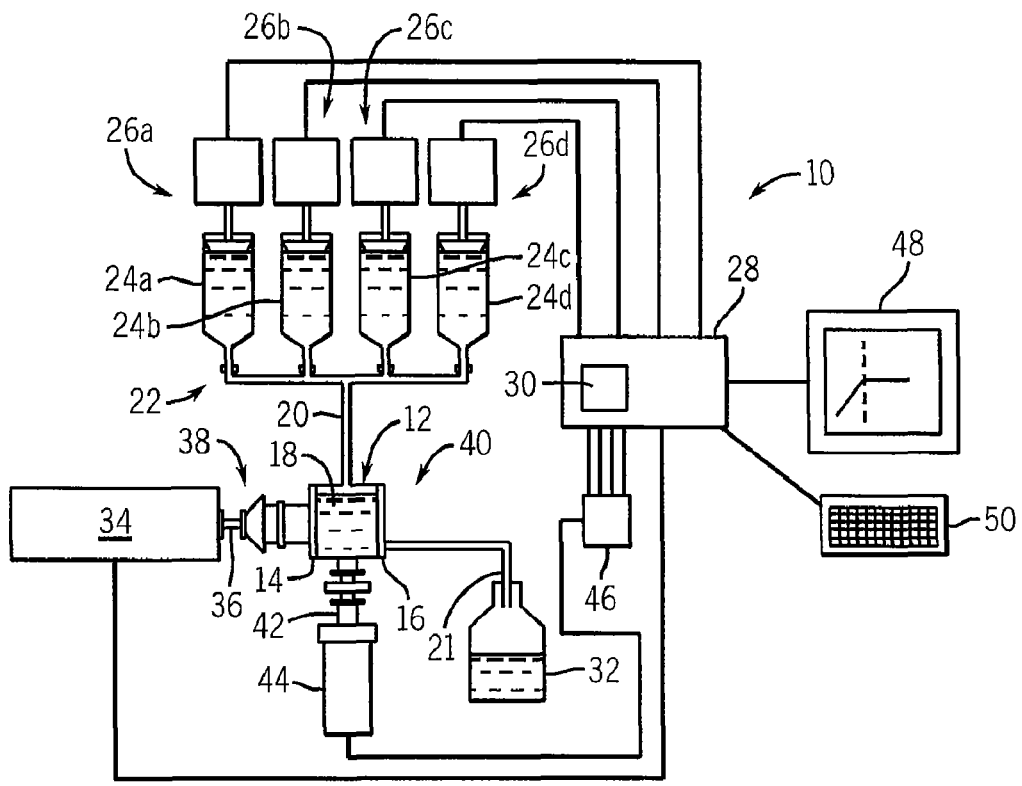
FIG. 1 is a schematic representation of an instrument of the present invention such as may provide for automated measurement of solvent solute mixtures in various concentrations under the control of a computer system.

Referring now to FIG. 1, an instrument 10 for evaluating solvent quality for a particular solute includes a sample chamber 12 having a transparent entrance window 14 and exit window 16 surrounding a sample volume 18. Solvent/solute solutions may be introduced into the sample chamber 12 through entrance conduit 20 and subsequently flushed into a receiving receptacle 32 through exit conduit 21.

The entrance conduit 20 may attach to a manifold 22 connecting it with a plurality of reservoirs 24a-24d (only four shown for clarity) each of which, for example, may be chambers of different syringe pumps 26a-26d. Syringe pumps 26 may be individually actuated by computer 28 according to a stored program 30 as will be described. Before operation of the instrument 10, each of the reservoirs 24a-24d will be loaded with solutions having different concentrations of solutes. When each syringe pump 26 is activated the contents of its given reservoir 24 are introduced through manifold 22 and entrance conduit 20 into the sample chamber 12. Other methods of filling the sample chamber 12 with successive samples may also be used, including, for example, manually operated syringes.

The instrument 10 includes a monochromatic laser 34 directing a beam 36 through collimating optics and filters 38 of the type well known in the art, through the entrance window 14 into the sample chamber 12 to fully illuminate the contained sample. A beam 42 of light scattered by the solute of the solution in the sample chamber 12 passes out of the exit conduit 21 to be received through additional collimating optics and filter 40 by a photomultiplier tube 44. The second beam 42 is received along an axis at a known angle with respect to beam 36, preferably 90°.

The photomultiplier tube 44 provides a signal to a counter 46 for each photon detected to provide for accurate assessment of the intensity of the scattered light. The signal from the counter 46 (a photon count) is received by the computer 28 which also controls the laser 34. The computer 28 may also communicate with an output device 48, such as a graphics display terminal, and an input device 50, such as a keyboard, allowing control and entry of data into the computer 28.

B. Discovery of Solvents

Referring now also to FIG. 2, the computer 28 executes a stored program 30 to provide for a semiautomatic assessment of solvents. At a first process block 52, a first solvent type is measured. At process block 54, the user is instructed, for example via a message on the output device 48, to load the reservoirs 24a-24d with different concentrations of the solute being investigated in a first solvent. The concentrations are preferably between 0.005 mg per milliliter and 0.5 mg per millimeter. The user is prompted to enter these concentrations into the input device 50 as well as an intrinsic quality of the solvent, preferably selected from: surface tension, surface energy, or Hildebrand parameter of the solvent. Preferably one reservoir (24a) will contain pure solvent for calibration purposes.

Referring now to process block 56, for each concentration of the selected solvent in reservoirs 24, the contained solution will be pumped into the sample chamber 12 (flushing out the previous material) and the laser 34 activated to make a measurement of scattering of the solution using the photomultiplier tube 44. The scattering measurement may be taken over a period of time and averaged to obtain high precision.

The number of photons detected by the photomultiplier tube 44 and counted by the counter 46 is then recorded by the computer 28. This value is compared to a previously made measurement of the pure solvent to obtain a Rayleigh scattering as indicated by process block 57.

At process block 58, the next concentration of solution (in the next reservoir 24) is then used to flush and fill the sample chamber 12 and the process block 57 is repeated (per loop process blocks 56 and 58) until the scatterings of each of the different concentrations for the given solvent have been characterized. Typically 7-10 different solute concentrations will be characterized for each solvent type. Optionally these and different concentrations will include concentrations above and below an anticipated solution saturation. Each solvent may be a single chemical species, such as N-methyl-2-pyrrolidone (NMP), or may be mixtures in different proportions of two or more chemical species, such as NMP and N-octyl-2-pyrrolidone (N8P), N-vinyl-2-pyrrolidone (NVP), or cyclohexyl-2-pyrrolidone (CHP), among others.

Figure 3:
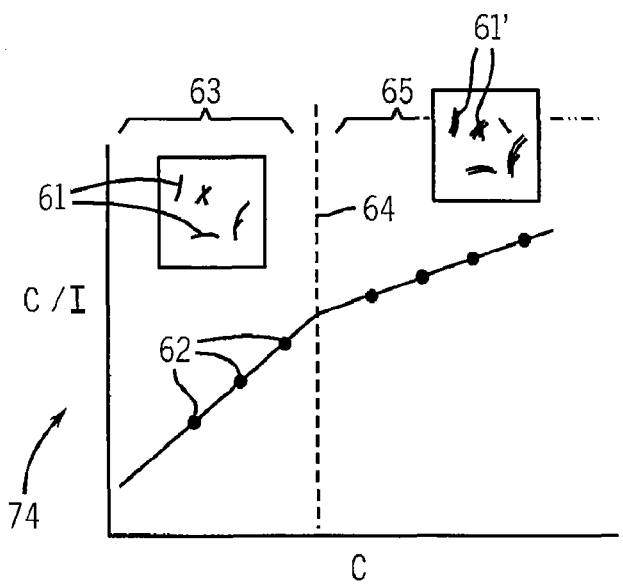
FIG. 3 is a chart showing a first set of data collected by characterization of two different solvents each at different levels of concentration.

As indicated by process block 60, the multiple measurements of Rayleigh scattering are then analyzed, for example, as shown in FIG. 3. In this analysis, each data point 62 representing a single measurement of the Rayleigh scattering will be plotted against the concentration. For analysis simplicity, the Rayleigh scattering is expressed as a concentration C divided by the change in Rayleigh scattering (shown in FIG. 3 as I), the latter being a difference between the intensity of the scattered light S for the given solution minus the scattered light $S_0$ for pure solvent as adjusted for machine constants (the latter related to the geometry of the measuring apparatus) and other constant factors that may be deduced or corrected through standard calibration techniques.

The analysis, indicated by process block 60, fits a function to the measured data to deduce a second virial coefficient ($B_2$). When the measured solutions all have concentrations below an expected saturation point of the solution and Rayleigh scattering is expressed as C/I, the function may be a line fit by "least-squares" or other fitting process. For polymer solvents acting on large molecules, the slope of this line provides an indication of the second virial constant of the solvent/solute system according to the following Debye light scattering equation (1):

$$\frac{C_{NT}}{S - S_0} = \frac{B_2}{K'} C_{NT} + \frac{1}{M_w K''} \qquad (1)$$

where:

$C_{NT}$ is the concentration of the solute;

S and $S_0$ are dimensionless numbers proportional to the scattering intensity of the solution and pure solvent respectively;

K and K' are instrument constants dependent on the spectrometer characteristics determined by calibration measurements of the spectrometer according to techniques well known in the art;

$B_2$ is the second virial coefficient; and $M_w$ is the molecular weight of the solute.

Once the second virial coefficient has been determined ($B_2$), it may be optionally converted to the Flory-Huggins parameter $\chi$ according to the following equation:

$$\chi = \tfrac{1}{2} - B_2 \bar{V}_2 \rho_{NT}^2 \qquad (2)$$

where:

$\bar{V}_2$ is the solvent molar volume, and $\rho_{NT}$ is the density of the solute.

Alternatively, the enthalpy of mixing $\Delta H_{Mix}$ may be determined according to the following equation:

$$\frac{\Delta H_{Mix}}{V_{Mix}} = \chi \frac{RT}{V_s} \phi(1 - \phi) \qquad (3)$$

where:

RT is the gas constant times absolute temperature, and $\phi$ is the solute volume fraction.

Generally, macromolecule solutes such as nanotubes will be thermodynamically soluble when the Gibbs free energy of mixing $\Delta G_{Mix}$ is negative. The Gibbs free energy is described by the following equation (4):

$$\Delta G_{Mix} = \Delta H_{Mix} - T \Delta S_{Mix} \qquad (4)$$

where:

$\Delta S_{Mix}$ is the entropy of mixing. For solutes with large molecular weight and/or high rigidity there will be an extremely small entropy of mixing $\Delta S_{Mix}$. For this reason thermodynamic solubility requires that $\Delta H_{Mix}$ is small.

Each of these expressions provides an indication of the solvent quality with respect to the particular solute. Note that these three measures of solvent quality $B_2$, $\chi$, and $\Delta H_{Mix}$ have different signs and therefore the best solvent will be indicated by a maximum for $B_2$ and a minimum for $\chi$ and $\Delta H_{Mix}$. These points of greatest solvent quality (regardless of the measure) will be termed "local extremes" being either a local maximum or a local minimum as context requires.

Referring still to FIGS. 1, 2 and 3, optionally, a range of concentrations of the solutes 61 in the solutions of reservoirs 24 may be used which span an aggregation point 64 of the solution. A first concentration range 63 below the aggregation point 64 provides a range in which the solute 61 is fully dissolved with no centrifugal separation. In this first concentration range 63, there may be some aggregation of the solute 61 (in the case of carbon nanotubes) but it is thermodynamically unstable and thus temporary. A second concentration range 65 above the aggregation point 64 provides a range in which the solute 61' begins to precipitate or form stable aggregations.

The present inventors have determined that the change in the Rayleigh scattering as a function of concentration can accurately reveal the aggregation point 64 of the solution and, in particular, when a solute of large molecules such as carbon nanotubes begins to aggregate. This aggregation point can be difficult to determine simply by looking for precipitate.

In one embodiment, the slope of the C/I line (with respect to concentration (C)) changes at the point where the solution passes saturation. This aggregation point 64 may be identified visually by inspection of the points in a graph 74 (output on output device 48) or preferably by the fitting of two different lines to the data point 62 in the first and second concentration ranges 63 and 65. The intersection of these lines defines the aggregation point 64. As a practical matter, this fitting process may be done by dividing the data points 62 into an arbitrary upper and lower group. A line is fit to each group (for example by a least-squares process) and the quality of the fit assessed. A new division of the upper and lower group is then selected and this process repeated. The qualities of the line fits for each different grouping are then compared to determine the grouping that provides the best line fit for both groups. This grouping is then used for the determination of the aggregation point 64. This evaluation of the aggregation point 64 is shown by process block 66 of FIG. 2.

Figure 4:
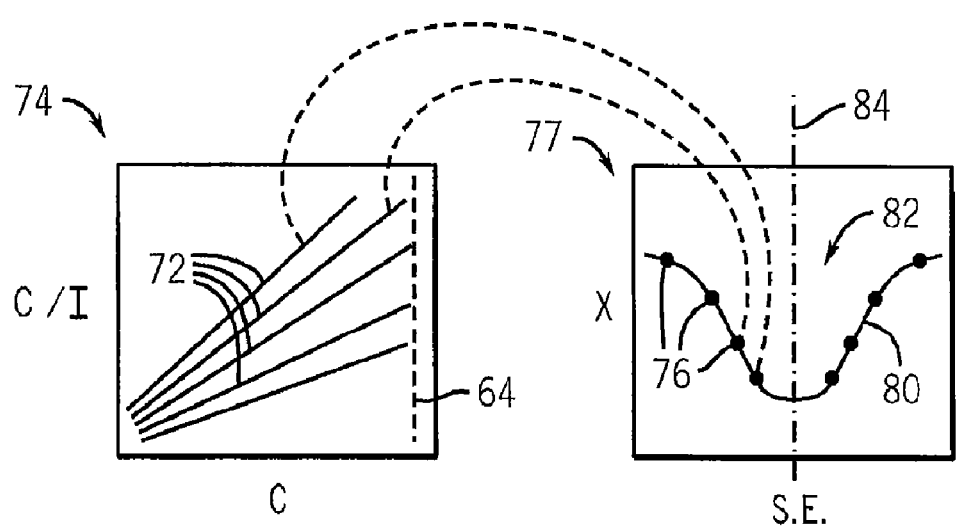
FIG. 4 is a diagram showing the conversion of the data of the chart of FIG. 3 to a solvent resonance curve of the present invention.

Referring now to FIGS. 2 and 4, at the conclusion of these data extraction steps of process blocks 60 and 66 for a given solvent, the stored program 30 loops (at process block 67) back to the process block 52 to repeat this process for the next solvent to be evaluated. Each solvent may be a single chemical species (such as NMP) or may be a mixture in different proportions of two or more chemical species (such as NMP and N8P or NVP).

At process block 70, and as indicated in FIG. 4, solvent quality 72 (for example: $B_2$, $\chi$, or $\Delta H_{Mix}$) for each solvent may then be plotted against an intrinsic property of the solvent. Specifically, the solvent qualities 72, here represented by multiple lines of different slopes in graph 74, provide a set of data points 76 defined by a solvent quality (being how effective this solvent is for the particular solute) and the intrinsic solvent property (for example, surface tension, surface energy or a Hildebrandt parameter value). These data points 76 provide a solvent quality graph 77 whose ordinate is solvent quality and whose abscissa is intrinsic property of the solvent. The intrinsic property of a solvent may be varied by mixing it with other materials. For example, the surface tension exhibited by a mixture of solvents will be equal to the mass weighted percentage of the individual solvent. In this case, changing the mass weighted percentages can change or tailor the surface tension of the solvent.

A curve 80 may be fit to these data points 76 to reveal a solvent resonance 82 being either a peak or trough (depending on the selection of the measure of solvent quality) in the curve 80. The extreme point 84 of the solvent resonance 82 (being either a local maximum or a minimum) indicates an optimal value for the intrinsic property of the solvent and may be output as indicated by process block 86 to the output device 48 described above. Once determined, the extreme point 84 may be used to investigate other materials having the intrinsic property of the extreme point 84. The actual solvent quality may then be verified using the process described above.

Figure 5:
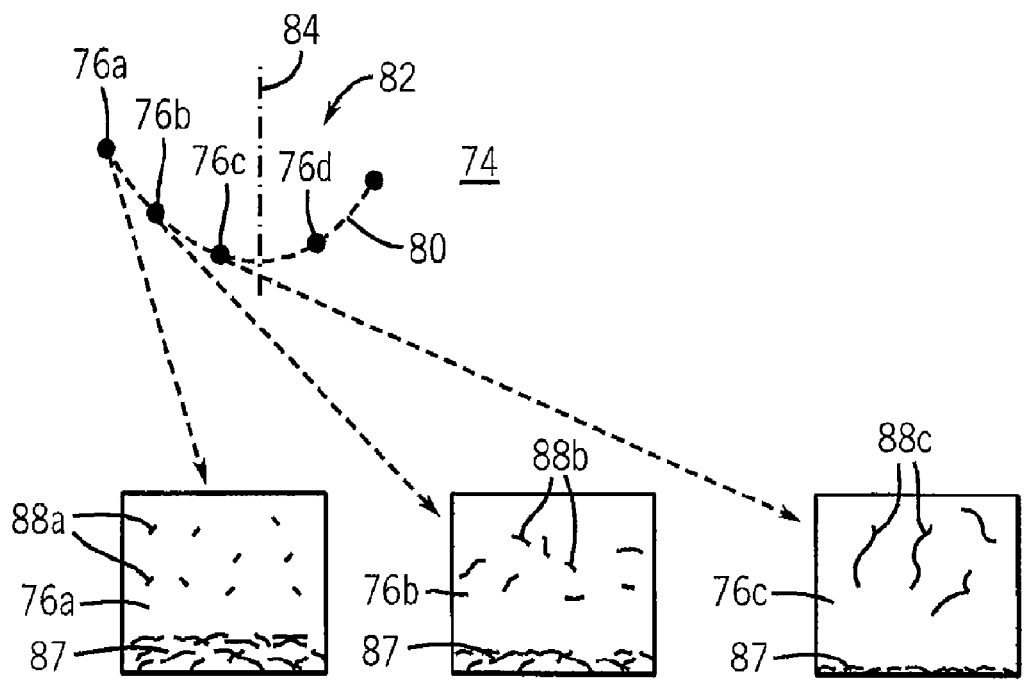
FIG. 5 is a fragmentary detail of a portion of the solvent resonance curve of FIG. 4 showing a use of the different solvents on the curve to perform solvent-based fractional extraction of macromolecules.

Referring now momentarily to FIG. 5, the location of the extreme point 84 will typically not be coincident with any of the data points 76, and the curve fitting process will allow a more precise determination of the intrinsic property of the optimal solvent beyond the granularity provided by the particular solvents chosen for measurement. The curve fitting may use standard mathematical techniques known in the art.

Figure 6:
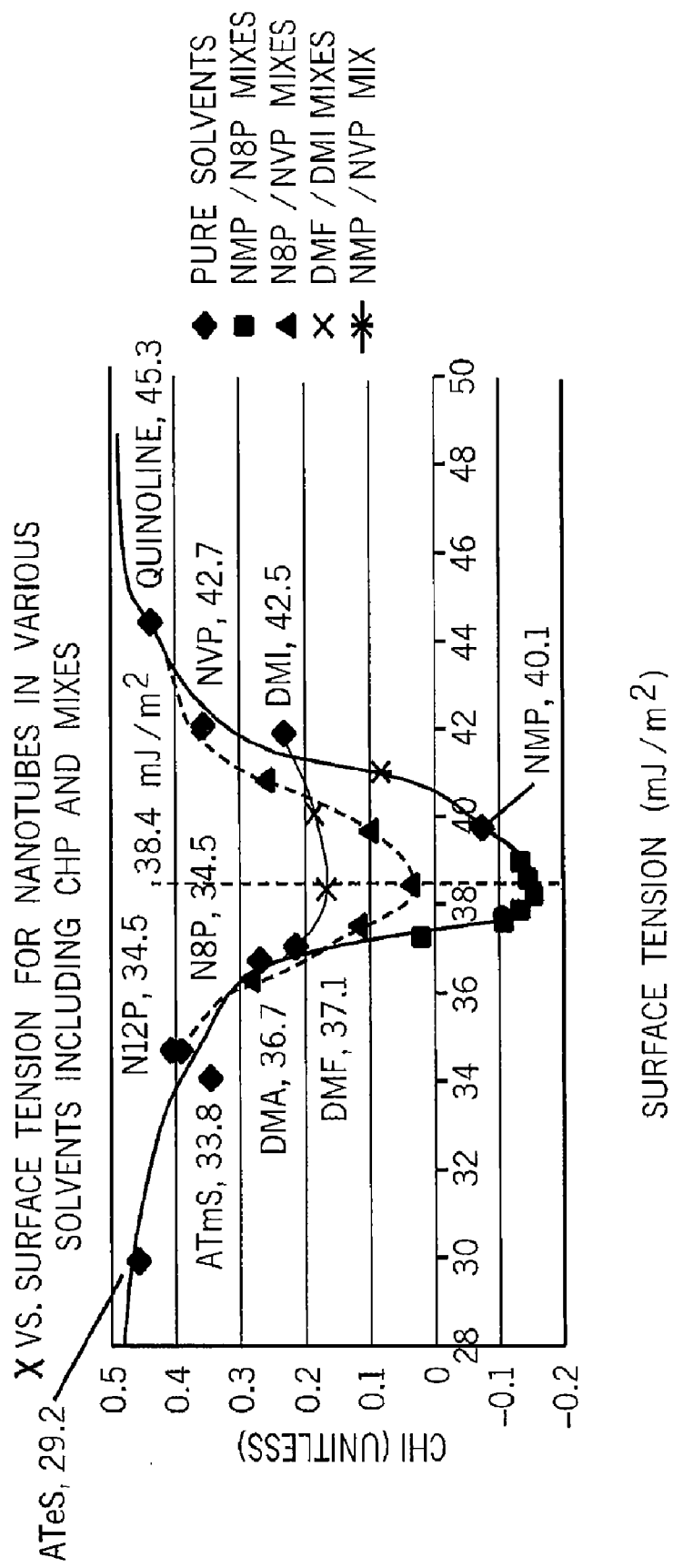
FIG. 6 is an experimentally produced plot of a solvent resonance per the present invention for single walled carbon nanotubes showing $\chi$ (chi) plotted against surface tension for variety of solvents and solvent mixtures.

Referring to FIG. 6, an actual solvent resonance 82 may be relatively sharp so that small changes in intrinsic property of the solvent (in this case NMP/N8P mixtures) can have significant effects on the solvent quality. In this case, the difference between the solvent quality of the solvent NMP and the solvent quality of the best NMP/N8P mixture represents approximately a threefold improvement of solvent quality. It is likely that improvements in solvent quality can be obtained by solvents more closely matching the ideal intrinsic property.

C. Example Solvents

Example Ia

Carbon Nanotubes

Referring to the following Table I, the present inventors have used this technique to evaluate the bundling point or dispersion limit for single-walled nanotubes (SWNT) and multi-walled nanotubes (MWNT) in a solvent of NMP. Referring also to FIGS. 2 and 3, the data representing the light scattering of various concentrations of both SWNT and MWNT in NMP is graphically illustrated. The data plotted against the concentration shows the two slopes of the data located on either side of the bundling point or dispersion limit for the solute in NMP.

Figure 24:
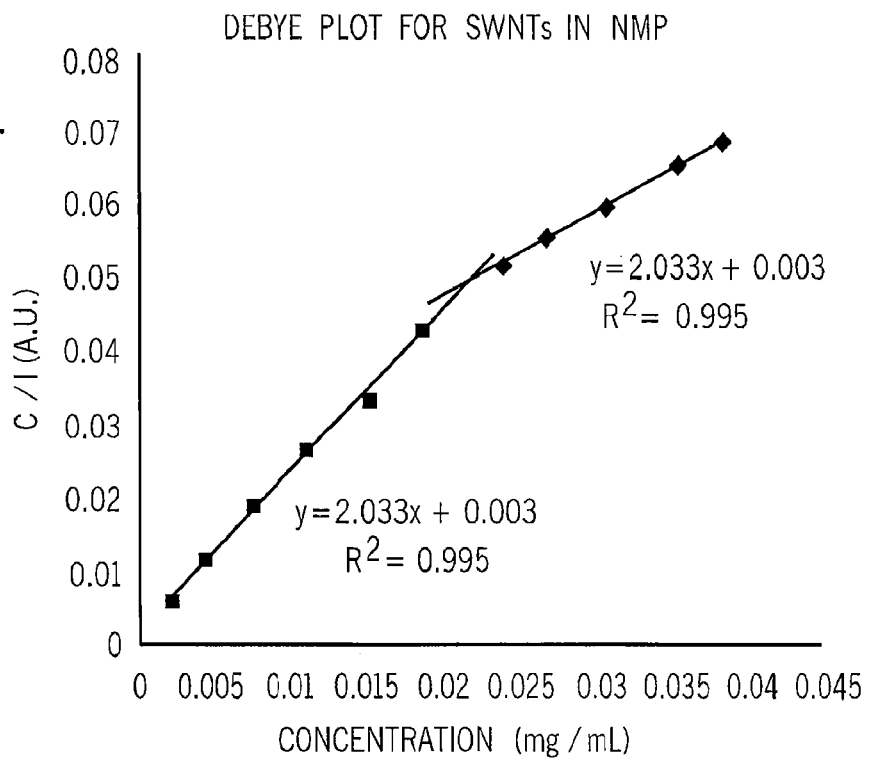
FIG. 24 is a graph showing a set of light scattering data plotted versus concentration for single walled nanotubes in NMP.
Figure 25:
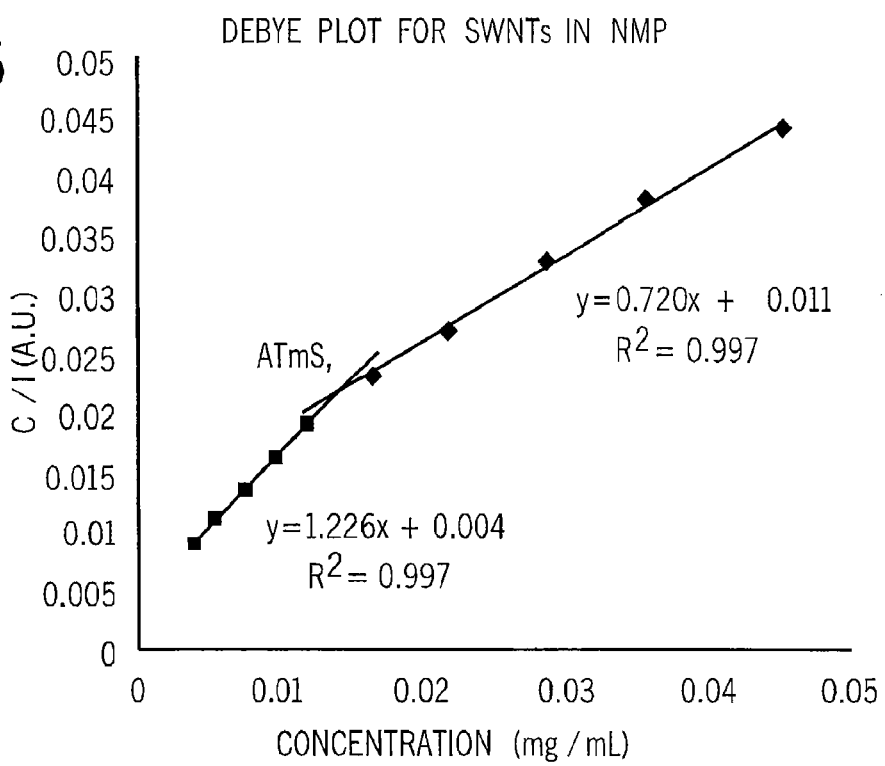
FIG. 25 is a graph showing a set of light scattering data plotted versus concentration for multiwall nanotubes in NMP.

Also, the data used to form the plots in FIGS. 24 and 25 can be utilized in the equations identified above to determine one or more of the various solvent quality values for the solvent. For the data in FIGS. 24 and 25, the determination of the bundling point and the solvent quality values of the second virial coefficient $B_2$ and Chi $\chi$ are represented in Table I as follows:

TABLE I

| solute/ solvent | $B_2$ (mol ml/g$^2$) pre-saturation | post-saturation | Aggregation Point (mg/ml) | Chi pre-saturation | post-saturation |
|---|---|---|---|---|---|
| SWNT/ NMP | .001782 | .000935 | .02161 | −.0782 | .0877 |
| MWNT/ NMP | .001277 | .000683 | .01383 | .0771 | .132 |

Figure 26:
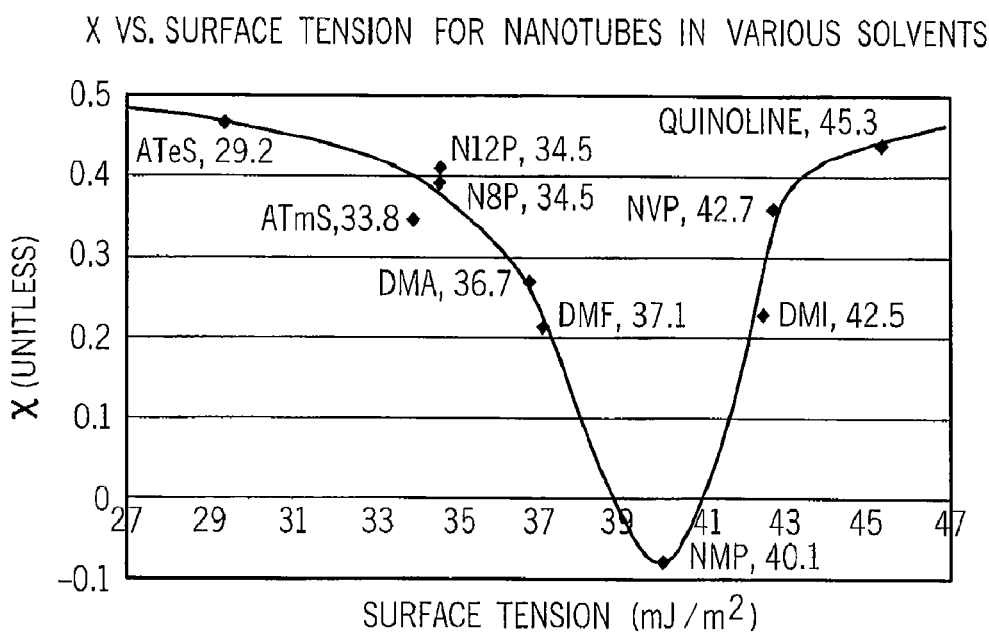
FIG. 26 is a graph showing a first solvent quality value calculated from data of the chart of FIG. 24 against a first intrinsic property for multiple pure solvents and forming a solvent resonance curve for single walled nanotubes.

With these solvent quality values, and other solvent quality values for other solvents tested at various concentrations of SWNT or MWNT in a similar manner, a plot can be created for these solvent quality values versus the intrinsic property of each of the solvents. The result of this plot is shown in FIG. 26, which illustrates the relation of the solvent quality value $\chi$ versus the intrinsic property of surface tension for each of the various solvents. This plot shows a clear resonance at a surface tension of approximately 40 mJ/m$^2$. Also, looking at the values on the plotted curve of FIG. 26 that intersect the line for a $\chi$ value of approximately zero, which indicate that those solvents at or below this value are capable of forming a true thermodynamic solution with the solute, in this case SWNT and MWNT, the values for the surface tension of those solvents of interest as being able to form a thermodynamic solution (i.e., having a value of $\chi$ less than about 0.01) are between approximately 37 mJ/m$^2$ and 41 mJ/m$^2$.

Example Ib

Carbon Nanotubes

To attempt to arrive at an optimal solvent that has an intrinsic property closer to the calculated resonance from the plot shown in FIG. 4, it is also possible to provide other solvents and solvents formed of mixtures of solvents. Referring now to FIG. 5, a plot similar to FIG. 26 is illustrated in which the solvent quality values in the form of $\chi$ for mixtures of various solvents calculated according to the above procedure are plotted versus the surface tension for each of those mixtures. Some of the values for the particular solvents and mixtures of solvents of interest, such as NMP, N8P, cyclohexyl-2-pyrrolidone (CHP), and N-ethyl-2-pyrrolidone (NEP) and the ionic liquid (1-Ethyl-3-methylimidazolium acetate (C8H14N2O2)) commercially available from BASF under the tradename BASF BASIONIC BC01, are shown below in Table II:

TABLE II

Measured Values of SWNT and MWNT in Various Solvents

| Solute | Solvent (mixture ratio) | Dispersion Limit | Surface Tension (room temperature and pressure) | Chi Value ($\chi$) |
|---|---|---|---|---|
| Single-wall nanotubes (SWNT) | CHP/NEP (5:1) | 0.232 mg/ml | 38.4 mj/m$^2$ | −0.348 |
|  | CHP | 0.16 mg/ml | 38.8 mj/m$^2$ | −0.3 |
|  | NMP/N8P | 0.058 mg/ml | 38.4 mj/m$^2$ | −0.15 |
|  | NMP | 0.0216 mg/ml | 40.1 mj/m$^2$ | −0.0746 |
|  | BASF BASIONIC BC01 (1-Ethyl-3-methyl-imidazolium acetate) | — | 42.17 mj/m$^2$ | 0.345 |
| Multi-wall nanotubes (MWNT) | NMP | 0.0138 mg/ml | 40.1 mJ/m$^2$ | 0.0771 |

Single-wall carbon nanotubes (SWNT) were dissolved in different mixtures of NMP and N8P providing nearly three times as much solvency as obtained in pure NMP. As shown in FIGS. 6-10, the present instrument has enabled the determination of solvents far improved over those currently known including the solvents of NMP.

The solvents provide three times as much solubility measured in maximum concentration before saturation than existing solvents and may be characterized by having a chi value less than 0.01. For the purpose of surface tension, the solvents are within 1.0 mJ/m2 of the ideal value of 38.4 mJ/m2.

Figure 10:
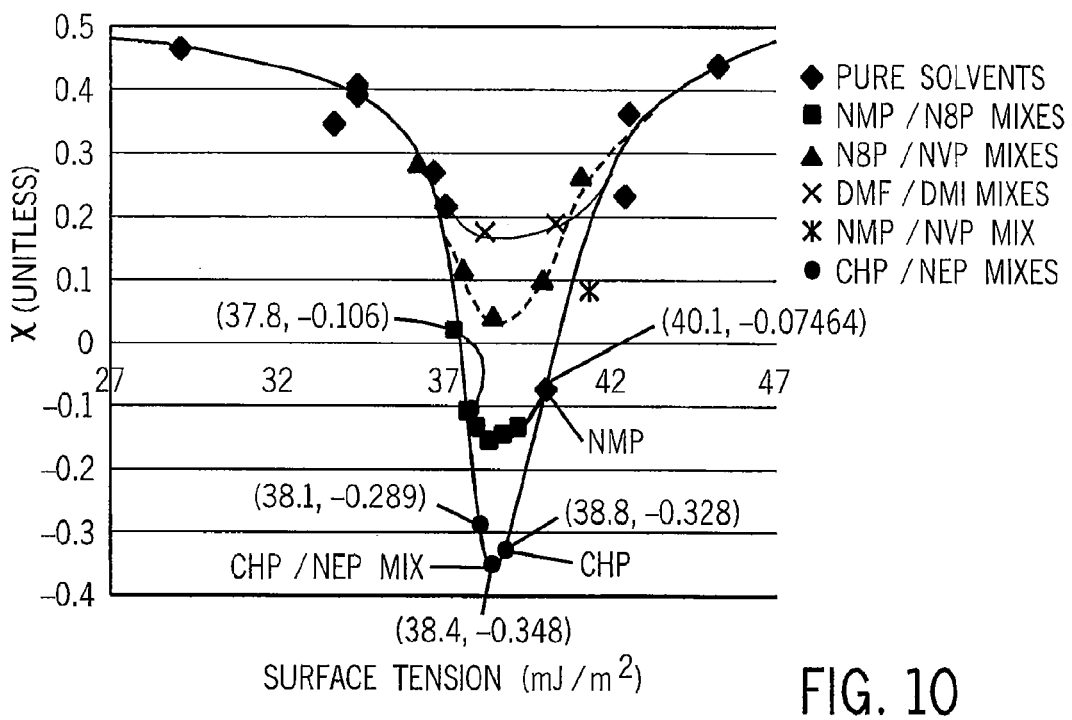
FIG. 10 is a figure similar to that of FIG. 6 showing mixtures of CHP and NEP for single wall carbon nanotubes.

As shown in the plot of FIG. 10 and in Table II above, the difference between the solvent quality of the solvent NMP and the solvent quality of the best NMP/N8P mixture represents approximately a twofold improvement of solvent quality, while the difference between NMP and CHP and/or the CHP/NEP mixture represents an over fourfold and almost fivefold increase in solvent quality.

Each of the solvent systems having a $\chi$ value of less than zero provides a true solution in thermodynamic equilibrium. Further, the calculated bundling point or dispersion limit indicates the maximum concentration of the solute at room temperature before an aggregation point where there is an abrupt increase in bundling of the solute. Note that the aggregation point of the solute is 10 times larger for the CHP/NEP solvent than for NMP alone.

Ionic liquids are organic compounds that are liquid at room temperature. They differ from most salts, in that they have very low melting points. They tend to be liquid over a wide temperature range, are not soluble in non-polar hydrocarbons, are immiscible with water, depending on the anion, and are highly ionizing (but have a low dielectric strength). Ionic liquids have essentially no vapor pressure. Most are air and water stable. The properties of the ionic liquids can be tailored by varying the cation and anion. Examples of ionic liquids are described, for example, in J. Chem. Tech. Biotechnol., 68:351-356 (1997); Chem. Ind., 68:249-263 (1996); and J. Phys. Condensed Matter, 5:(supp 34B):B99-B106 (1993), Chemical and Engineering News, Mar. 30, 1998, 32-37; J. Mater. Chem., 8:2627-2636 (1998); and Chem. Rev., 99:2071-2084 (1999), the contents of which are hereby incorporated by reference.

The organic nonaqueous ionic liquid solvent example above shows that ionic liquids can be found approximating the desired intrinsic properties. With proper selection and by modification of the temperatures of the solvent system, it is clear that ionic liquids may be closely tailored as macromolecule solvents.

As a result, the solvents identified in the present invention for use in forming true thermodynamic solutions with SWNT and MWNT may be characterized as having a $\chi$ value less than about 0.01. For the purpose of defining these solvents by their surface tension values as a result of the plot in FIGS. 26 and 10, the solvents are between about 37 mJ/m$^2$ and about 39 mJ/m$^2$ or more, preferably between about 38 mJ/m$^2$ and about 39 mJ/m$^2$ about the ideal calculated value of 38.4 mJ/m2. In addition, as shown by the data in Tables I and II, the solvents of the present invention can further be characterized as those solvents capable of forming solutions of SWNT or MWNT having a concentration of at least 0.05 mg/ml and preferably of at least 0.20 mg/ml and up to about 0.25 mg/ml.

The solvent resonance for solvents used for the carbon nanotubes can also be characterized by reference to chi or $\chi$ having a value of chi of less than −0.08 when measured with the pristine carbon allotropes and preferably between about 0.11 and about −0.4.

Figure 7:
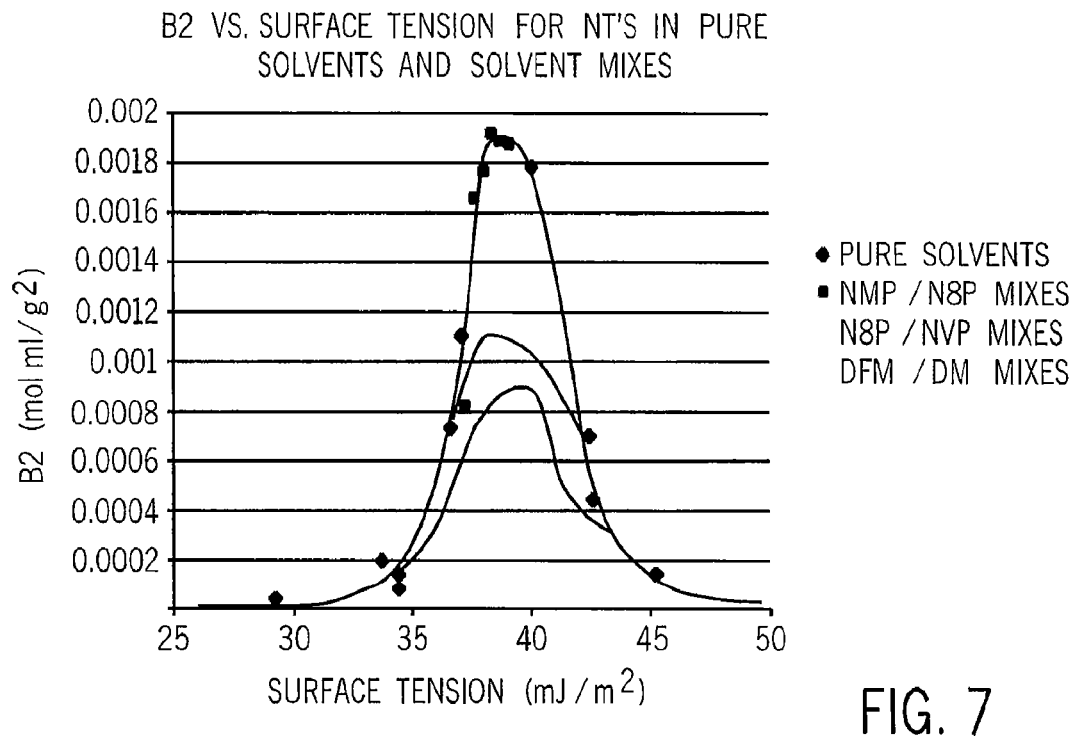
FIG. 7 is a figure similar to that of FIG. 6 showing the second virial parameter $B_2$ plotted against surface tension.

The solvent resonance for solvents used for the SWNTs can also be characterized, as shown in FIG. 7, by the curve plotted for the second virial coefficient B2 preferably providing a second virial coefficient greater than 0.0014 mol·ml/g2 for pristine carbon nanotubes and preferably a second virial coefficient between about 0.0016 mol·ml/g2 and at least about 0.0020 mol·ml/g2. In this plot, the resonance for the solvents appears over the same range as that determined using $\chi$ as the solvent quality, i.e., approximately at 37-41 mJ/m2.

Figure 8:
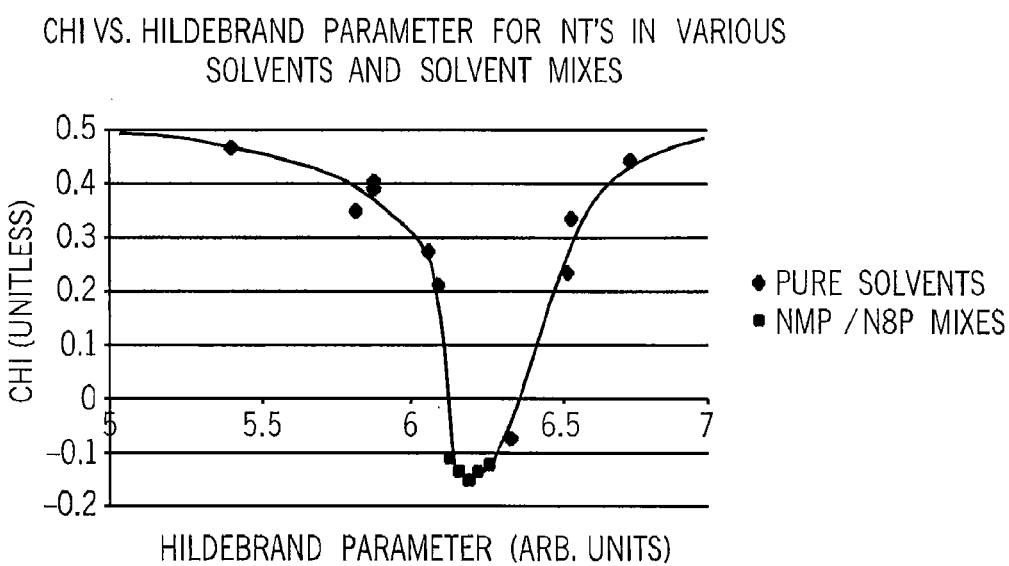
FIG. 8 is a figure similar to that of FIGS. 6 and 7 showing $\chi$ plotted against the Hildebrand parameter.
Figure 9:
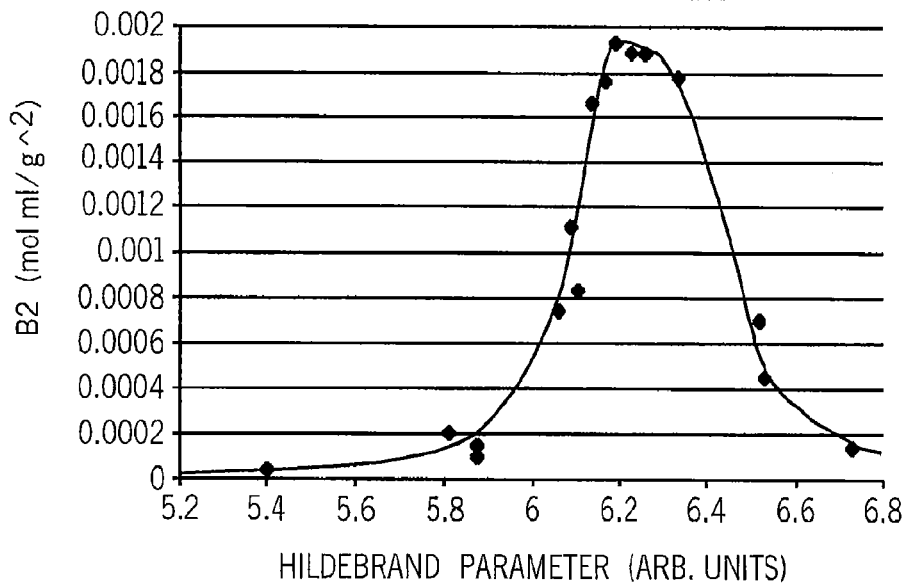
FIG. 9 is a figure similar to that of FIGS. 6, 7, and 8 showing the second virial parameter $B_2$ plotted against the Hildebrand parameter.

The solvent resonance shown by the curves in FIGS. 10 and 7 also appears when the intrinsic property is switched, as evidenced in FIGS. 8 and 9 showing the plots of $\chi$ versus the Hildebrand parameter, and the second virial coefficient versus the Hildebrand parameter, respectively. In this case, the solvent is characterized by a Hildebrand parameter of between about 6.0 and about 6.5 and preferably a Hildebrand parameter between about 6.2 and about 6.4. As a result, it is also expected that the solvent resonance for solvents used for the SWNT will also be borne out by curves plotted for other calculated solvent quality values, such as the enthalpy of mixing, $\Delta H_{Mix}$, versus the surface tension, or other intrinsic property values, such as the surface energy or Hildebrand parameter, for the various solvents.

Example Ic

Functionalized Carbon Nanotubes

Figure 29:
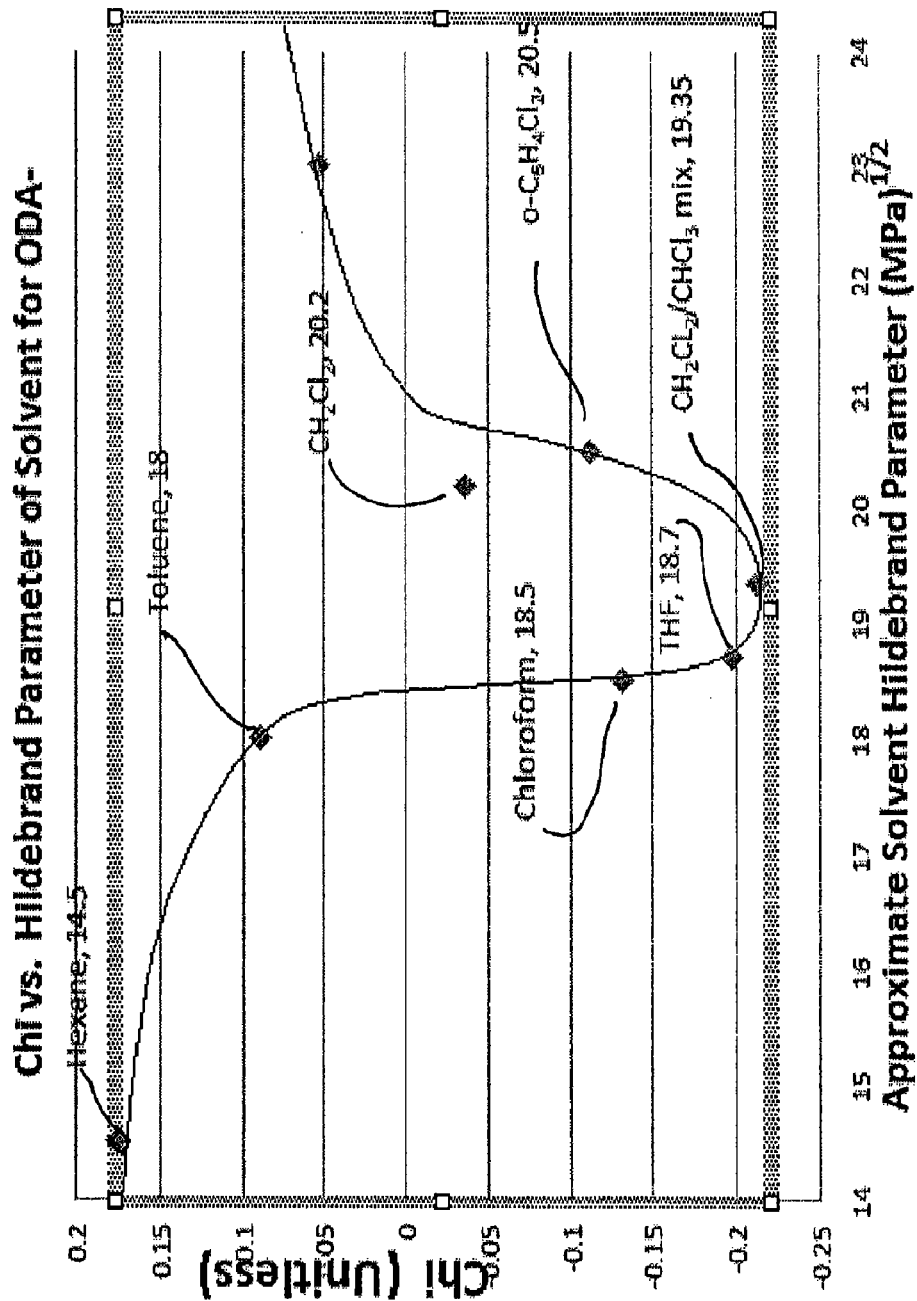
FIG. 29 is a figure similar to FIGS. 6, 8, 10, 11 22 and 26, showing ideal solvent properties for ODA functionalized nanotubes.
Figure 30:
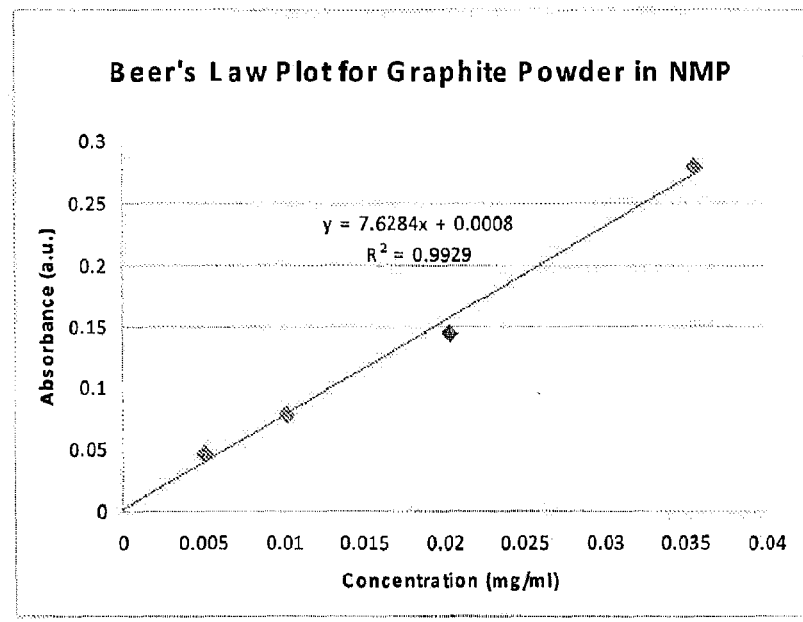
FIG. 30 is a graph of absorbance versus concentration for graphite powder dispersed in NMP to provide for a dispersion of transparent graphene plates.

Referring to FIG. 29, present technique also works with nanotubes functionalized with octyl decanoic acid (ODA). For example, ODA functionalized SWNT nanotubes have an optimum solvent/matrix Hildebrand Parameter of between 18-21 MPa$^{1/2}$ and an ideally near 19.5 MPa$^{1/2}$. Optimal solvents, for example, approximated by CH$_2$Cl$_2$/CHCl$_2$, achieve a value of $\chi$ less than about −0.2 while other solvents such as chloroform, THF and o-C$_6$H$_4$Cl$_2$ obtained values of $\chi$ less than zero all indicating true thermodynamic solvency. Thus the present invention works not only with pristine macromolecules but can be used to provide improved solvents or functionalized macromolecules. Optimally tuning composite material properties that utilize functionalized nanomaterials are an important embodiment of this invention because some covalent bonds to the matrix will optimize properties such as strength and matching the surface energy of both matrix and incorporant with further optimize properties.

Example IIa

Graphene

Referring to the following Table III, the present inventors have used this technique to establish the solvency of graphene in NMP and to evaluate the aggregation point for graphene in a solvent of NMP as follows:

TABLE III

| Solute/solvent | B$_2$ (mol ml/g$^2$) | | Aggregation Point (mg/ml) | Chi | |
|---|---|---|---|---|---|
| | pre-saturation | post-saturation | | pre-saturation | post-saturation |
| Graphene/NMP | .00045 | .000143 | .0520 | −0.0643 | 0.0828 |

Figure 23:
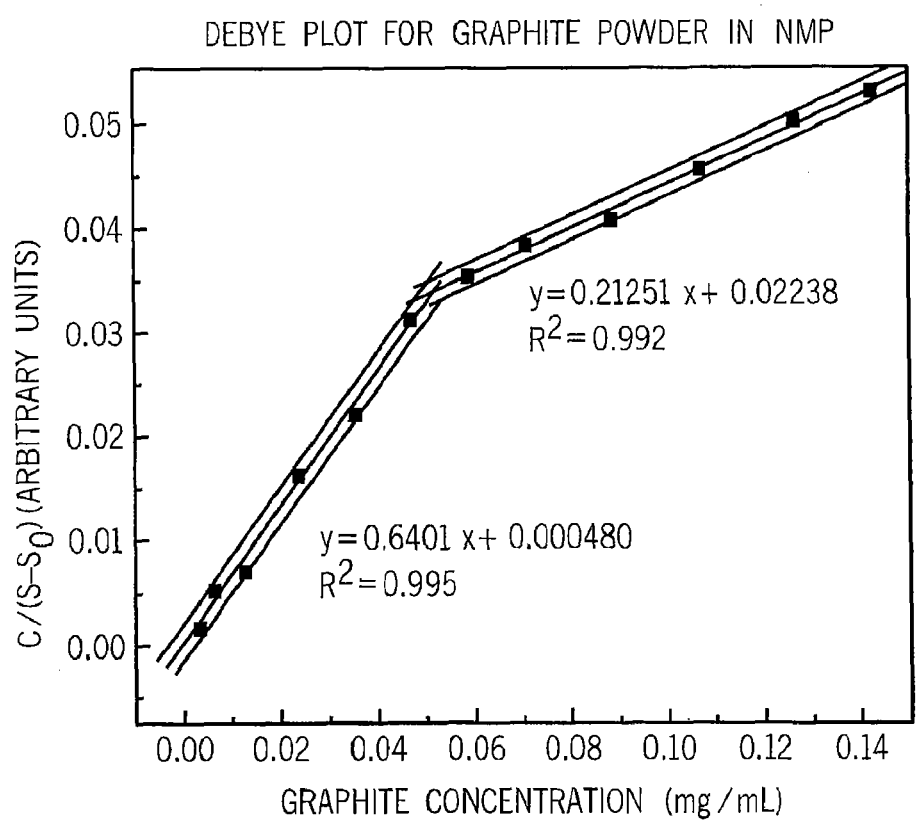
FIG. 23; a graph showing a set of light scattering data plotted versus concentration for graphite powder in NMP.

Two typical types of graphite a natural and a synthetic were used: Technical Grade Graphite from Sargent Chemical Company and a common, commercial 350 Mesh Mr. Zip Graphite Powder from AGS Corporation of Michigan. Samples were investigated of the solution above the aggregation point (at 0.05839 mg per milliliter) and below the aggregation point at (0.04656 mg per milliliter). Samples were deposited on clean silicon wafers and the NMP was allowed to evaporate in a vacuum. Using a Nanoscience EasyScan2 atomic force microscope, images of the samples were obtained. The sample below this aggregation point contained no apparent graphite aggregation whereas the sample above the aggregation point contained many large graphite aggregations that range from 15 to 100 nm in height and the hundreds to thousands of nanometers in width and length. A Debye plot of the Rayleigh absorption data is shown in FIG. 23. Graphene produced by this process with the sonic agitation has been demonstrated to include a substantial number of sheets that are one atomic layer thick (about 30%), chemically unmodified and defect free graphene.

The above techniques have been used to identify a desired surface tension range for a solvent of bulk graphite of between 36 and 43 surface tension units (mJ/m2). A 5:1 mixture of N-methyl-2-pyrrolidone (NMP) and octyl-2-pyrrolidone is near to this desired value of an intrinsic property for such a solvent.

Figure 11:
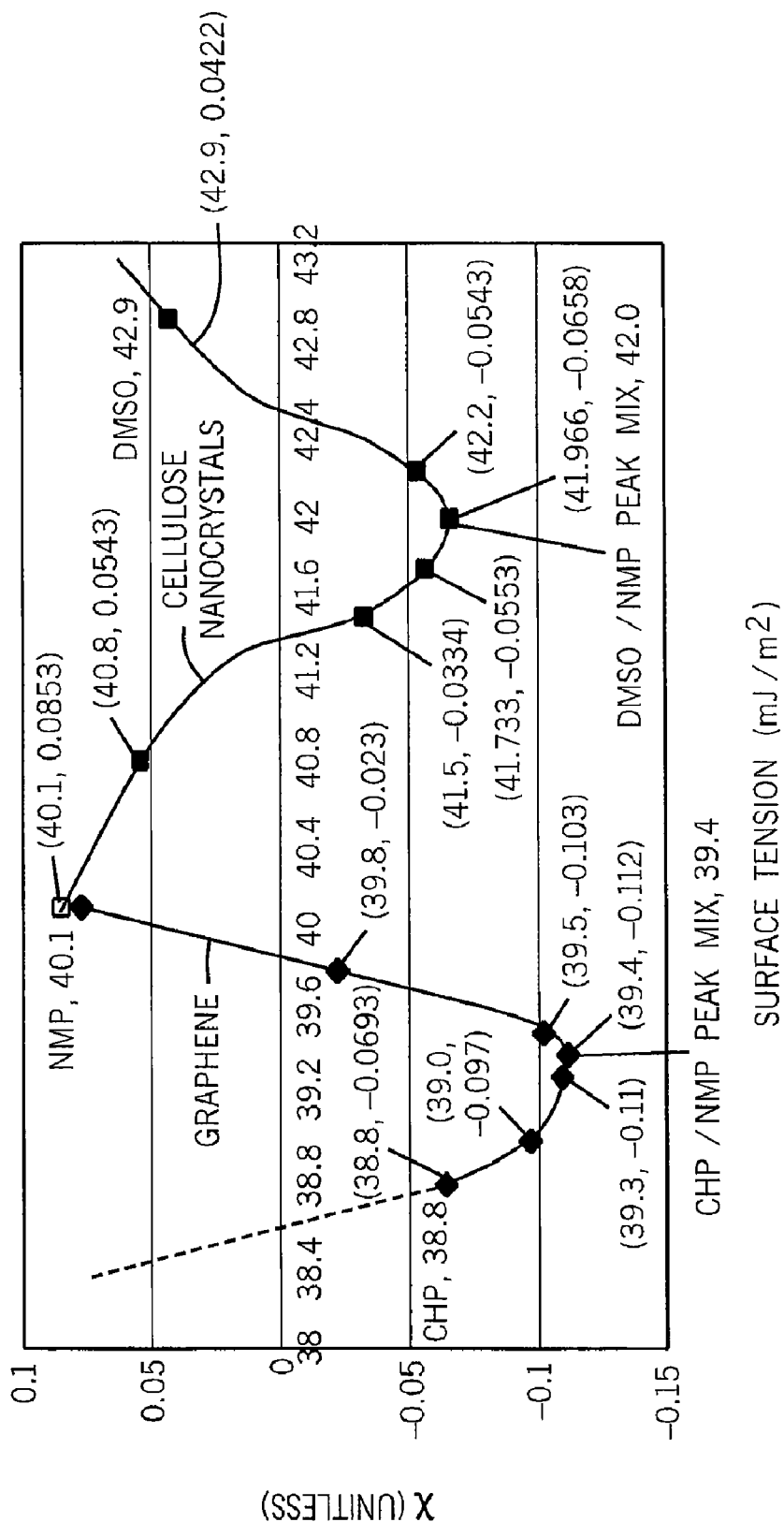
FIG. 11 is a figure similar to that of FIG. 6 showing solvents for graphene and cellulose nanocrystals as determined by the present invention.

In addition, other solvents have been investigated for graphene as follows and as shown in FIG. 11:

TABLE IV

Measured Values of Graphene in NMP

| Solute | Solvent (mixture ratio) | Dispersion Limit | Surface Tension (room temperature and pressure) | Chi Value ($\chi$) |
|---|---|---|---|---|
| Graphene | CHP/NMP (2:1) | 0.0824 mg/ml | ~39.4 mj/m² | <−0.112 |

Example IIb

Graphene

With these solvent quality values, and other solvent quality values for other solvents tested at various concentrations of graphene in a similar manner, a plot can be made for these solvent quality values versus the intrinsic property of each of the solvents.

Figure 22:
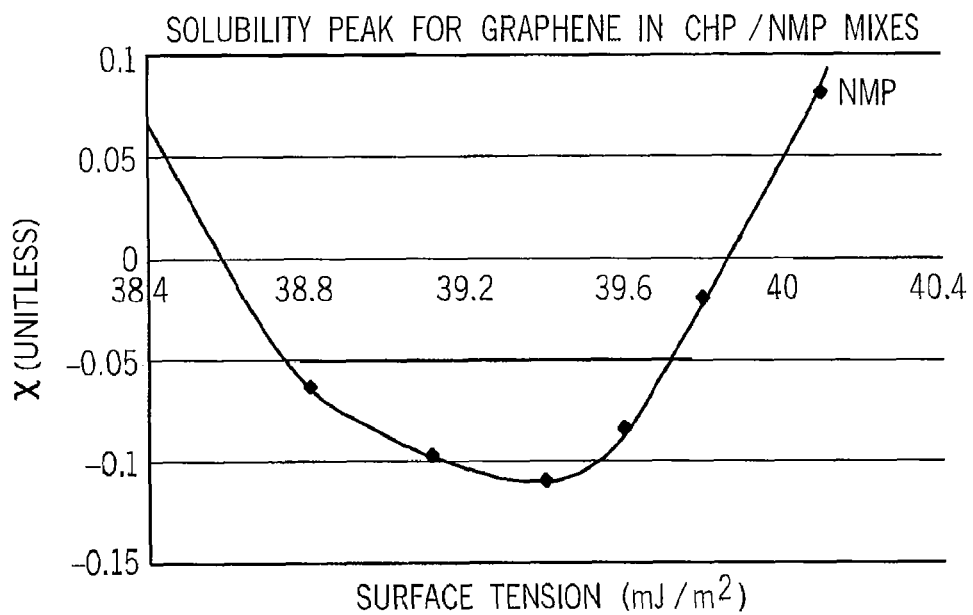
FIG. 22 is a graph showing a first solvent quality value calculated using the instrument of FIG. 1 and forming a solvent resonance curve for grapheme.

The result of this plot is shown in FIG. 11 or FIG. 22, which illustrates the relation of the solvent quality value $\chi$ versus the intrinsic property of surface tension for each of the various solvents. In particular, the above techniques have also been used to identify a desired surface tension range for a solvent of bulk graphite having a surface tension value of between 36 and 43 surface tension units (mJ/m2). This plot shows a clear resonance at a surface tension of approximately 39.4 mJ/m². Also, looking at the values on the plotted curve of FIG. 11 or FIG. 22 that intersect the line for a $\chi$ value of approximately zero, which indicate those solvents at or below this value are capable of forming a true thermodynamic solution with the solute, in this case graphene, the values for the surface tension of those solvents of interest as being able to form a thermodynamic solution (i.e., having a value of $\chi$ less than about 0.01) are between approximately 38.6 mJ/m² and 39.8 mJ/m².

More specifically, to attempt to arrive at a more optimal solvent that has an intrinsic property closer to the calculated resonance from the plot shown in FIG. 4, it is also possible to provide solvents formed of mixtures of solvents. Some of the values for the solvent formed as a mixture of NMP and cyclohexyl-2-pyrrolidone (CHP) are shown below in Table V:

TABLE V

Measured Values of Graphene in CHP/NMP

| Solute | Solvent (mixture ratio) | Dispersion Limit | Surface Tension (room temperature and pressure) | Chi Value ($\chi$) |
|---|---|---|---|---|
| Graphene | CHP/NMP (1:3) | | 39.8 mJ/m² | −0.023 |
| Graphene | CHP/NMP (3.8:2) | | 39.5 mJ/m² | −0.103 |
| Graphene | CHP/NMP (2.1:1) | 0.0824 mg/ml | ~39.4 mJ/m² | <−0.112 |
| Graphene | CHP/NMP (1.8:1) | | 39.3 mJ/m² | −0.110 |
| Graphene | CHP/NMP (3:1) | | 39.0 mJ/m² | −0.097 |
| Graphene | CHP | | 38.8 mJ/m² | −0.0643 |

The results illustrate that the 2:1 mixture of CHP/NMP is near to this desired value of an intrinsic property for such a solvent. As shown in the plot of FIG. 11 and in Table V above, the difference between the solvent quality of the solvent NMP and the solvent quality of the best CHP/NMP mixture represents approximately a twofold improvement of the calculated bundling point or dispersion limit, indicating the maximum concentration of the graphene at room temperature before an aggregation point where there is an abrupt increase in bundling or agglomeration of graphene. Each of the CHP and CHP/NMP solvent systems, having a $\chi$ value of less than zero, provides a true solution in thermodynamic equilibrium.

As a result, the solvents identified in the present invention for use in forming true thermodynamic solutions with graphene may be characterized as having a $\chi$ value less than about 0.01. For the purpose of defining these solvents by their surface tension values as a result of the plot in FIG. 11, the solvents are within about ±1.0 mJ/m2, or more preferably within about ±0.6 mJ/m2 of the ideal calculated value of 39.4 mJ/m2. In addition, as shown by the data in Tables IV and V, the solvents of the present invention can further be characterized as those solvents capable of forming solutions of graphene having a concentration of at least 0.05 mg/ml and up to about 0.10 mg/ml.

It is also expected that the solvent resonance for solvents used for graphene will also borne out by curves plotted for other calculated solvent quality values, such as the second virial coefficient B2 or the enthalpy of mixing, $\Delta H_{Mix}$, versus the surface tension or other intrinsic property values, such as the surface energy or Hildebrand parameter, for the various solvents.

Example III

Referring to the following Table VI, the present inventors have used this technique to establish the solvency of cellulose nanocrystals in DMSO and NMP and to evaluate the aggregation point for cellulosic nanocrystals as also shown in FIG. 11:

TABLE VI

| Solute | Solvent (mixture ratio) | Dispersion Limit | Surface Tension (room temperature and pressure) | Chi Value ($\chi$) |
|---|---|---|---|---|
| Cellulosic nanocrystals | DMSO/NMP (2:1) | ~.09 mg/ml | 42.0 mj/m² | −0.06 |

It is believed that other pyrrolidones may also be useful as solvents including propyl-, butyl-, cyclobutyl-, pentyl-, cyclopentyl-, hexyl-, heptl- and any alkyl pyrrolidone or substituted pyrrolidone having a side chain that makes chi negative.

D. Assessment of Molecular Interaction

Figure 12:
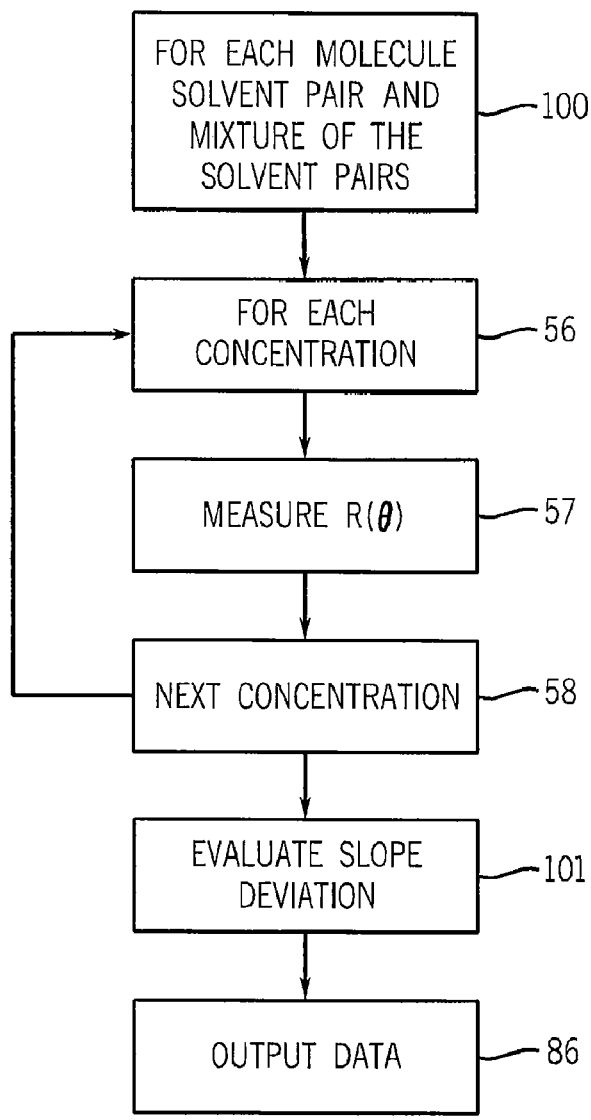
FIG. 12 is a figure similar to that of FIG. 2 showing a flow chart for use of the instrument of the present invention for the quantification of molecular interactions.
Figure 13:
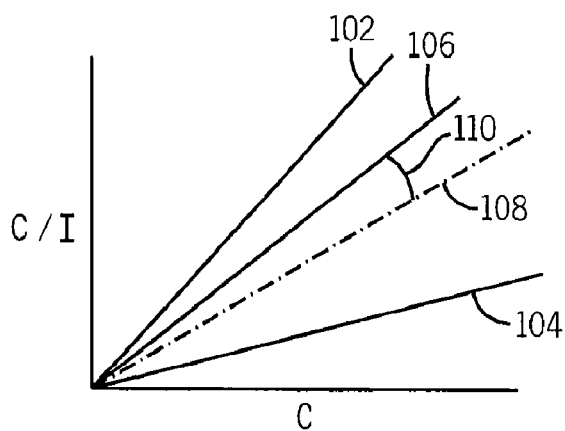
FIG. 13 is a figure similar to that of FIG. 4 showing determination of molecular interaction by measuring deviation from a median Rayleigh scattering line.
Figure 14:
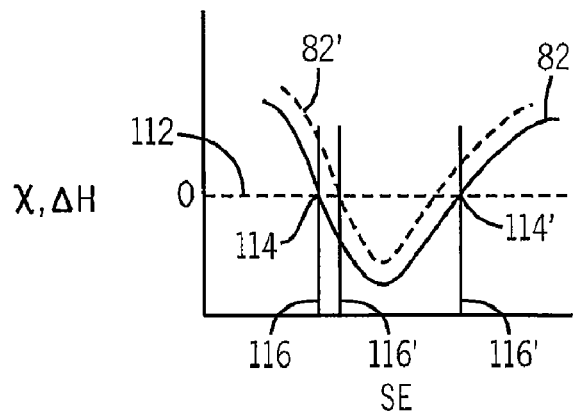
FIG. 14 is a figure similar to that of FIGS. 6-11 showing use of the solvent resonance obtained by the present invention to identify solvents for crystallization.
Figure 15:
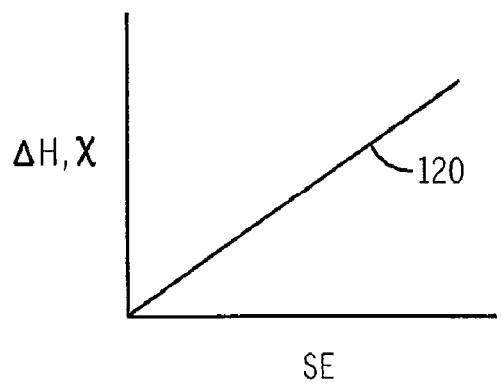
FIG. 15 is a figure similar to that of FIG. 13 showing use of the instrument for determining Gibbs free energy of complex solutions.
Figure 16:
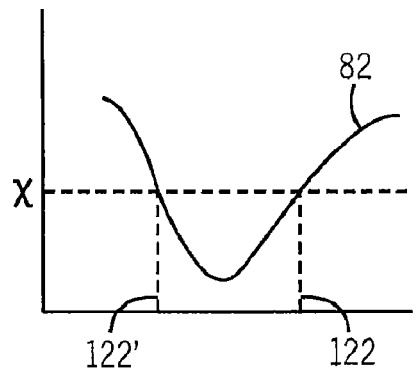
FIG. 16 is a figure similar to that of FIG. 14 showing use of the solvent resonance to deduce surface energies in applications where conventional surface energy techniques are difficult or inapplicable.
Figure 17:
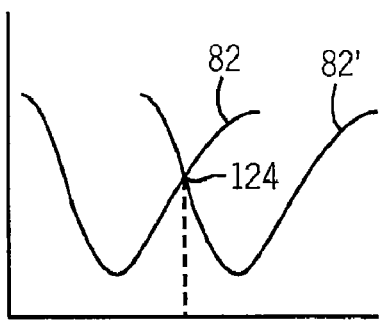
FIG. 17 is a figure similar to that of FIG. 14 showing the use of two solvent resonances to identify an optimum joint solvent.

Referring now to FIG. 12, the present instrument may also output data quantifying an affinity between different molecular species, for example, between antibodies and antigens or other proteins. In this application, as indicated by process block 100, each molecule together with its solvent (the same or different) is analyzed in different concentrations and Rayleigh scattering measured as indicated by process blocks 56, 57, and 58 described previously. As indicated by FIG. 13, measurements over these concentrations will produce sloped lines 102 and 104 for the molecule/solvent pairs. As also indicated by process block 100, a mixture of the two molecules and their solvents (which may be identical) are also processed per process block 56, 57, and 58 to produce sloped line 106.

A median line 108 may then be determined under an assumption of no molecular interaction as a simple mathematical averaging of lines 102 and 104 according to the relative amount of each molecule in the mixture. A deviation 110 in slope between the median line 108 and the mixture line 106, as measured at process block 101 indicates an interaction between the molecule species. Generally a deviation upward from line 108 indicates a molecular attraction and a deviation below line 108 represents a molecular repulsion. A graph or quantitative data may be output at process block 86. It is believed that this process can be extremely sensitive to degrees of molecular affinity or repulsion.

It will be understood that in addition, a family of deviations 110 may be developed by changing one of the molecules to thus provide a measurement of variations in affinity or repulsion as a function of the molecule being varied. This system may be useful in the medical arena for detecting antibody antigen binding as well as attraction or repulsion short of such a binding.

E. Development of Crystallization Solvents

The ability to accurately characterize $\chi$ as a function of an intrinsic property of the solvent permits identification not only of the best solvents but also solvents that have a relatively low delta $\Delta H_{Mix}$ such as may be desirable for crystallization of molecules, for example, proteins. In this case, a $\chi$ value 112 corresponding to zero $\Delta H_{Mix}$ is identified at points of intersection 114, 114' between the $\chi$ value and a resonance curve 82 for the molecule to be crystallized in a solvent to be used in the crystallization. The points of intersection 114 and 114' identify intrinsic characteristics 116, 116' of solvents that can be used to identify solvents that will produce the desired low $\Delta H_{Mix}$. During the crystallization process, the pressure or temperature r may be controlled to shift the resonance curve 82 up or down as indicated by resonance curve 82' to control the crystallization process or to bring a solvent (at intrinsic characteristics 116') that is not at the point of intersection 114, 114' better into alignment with a low $\Delta H_{Mix}$ value.

F. Measurement of Gibbs Free Energy

Measurement of the Gibbs free energy can be useful, for example, in environmental systems where it is desirable to determine whether pollutants will be bound in the environment or will migrate freely through it. In this case, a scattering line 120 may be developed as before by varying the concentration of the pollutant in a complex environmental mixture, for example, water plus organic materials. This scattering line 120 provides a measurement of $\Delta H_{Mix}$ which can be used to derive Gibbs free energy according to the equation (4) above, in which $\Delta H_{Mix}$ is known from the slope of line 120, temperature (T) is measured and $\Delta S_{Mix}$ assumed to be small or zero for relatively large and stiff molecules such as carbon nanotubes. This approach may be used, for example, to investigate the environmental impact of nanoparticles such as nanotubes or the like.

G. Measurement of Surface Energy

The present invention may also provide precise measurement of surface energy or surface tension particularly in systems where conventional surface energy measurements, for example contact angle, are impractical because of size or other impediments. Such surface energy measurements involve determining, for example, $\chi$ by measuring the slope of the line produced by process blocks 56, 57, and 58, described above respect to the materials defining the surface energy in question. The $\chi$ value may then be applied to a resonance curve 82 constructed from measurements of solvent systems having a shared component (either the solute or solvent) where the surface energy is already known or may be readily characterized. A smooth curve may be fit to discrete measurements by a curve fitting process. The intersection of the $\chi$ value and the resonance curve 82 presents two possible surface energy measurements 122 and 122', one of which can be usually discarded by inspection.

H. Discovery of Joint Solvent Systems

It will be understood that the present invention may be used to characterize the optimal solvent for two different materials, for example, when a composite material is to be constructed of two materials such as graphene and carbon nanotubes. Here, multiple resonance curves 82 and 82' are developed as described for each of the different molecular solutes for a range of different solvents as described above. For example, solvent resonance 82 may be for carbon nanotubes and solvent resonance 82', may be for graphene. By superimposing the resonances 82 and 82' on the same horizontal scale, an optimal intrinsic property 124 for a jointly effective solvent may be developed. In this way a multiple nanoparticles such as graphene and carbon nanotubes may be combined in thermodynamic equilibrium and may prove structurally synergistic. The resonance curves 82 and 82' also allow a trade-off to be effected where the solvent properties for one material are better than the other.

I. Applications of Discovered Solvents

1. Separation and Purification

Referring again to FIG. 5, accurate characterization of the solvent quality of multiple solvents for a given solute, as provided by the data of graph 77, may be used not only to identify an improved solvent but also to create improved separation of mixed solutes, for example, mixtures of carbon nanotubes of different sizes or different numbers of walls. This separation may use the different solvents (including varying ratios of two solvents having different solvent qualities) to selectively dissolve macromolecules of different sizes taking advantage of a slight dependency between molecule size and solubility of the molecule. Alternatively, a solution of a mixture of molecules may have the quality of its solvent altered by mixing with another solvent to selectively precipitate molecules from solution.

As shown in FIG. 5, a mixture 87 of nano-structure molecules may be exposed to the first solvent of data point 76a to promote the dissolution of small macromolecules 88a, the solvent of data point 76a providing less solubility of larger macromolecules. Once in solution, these smaller macromolecules may be decanted together with the solvent and thereby isolated from the other molecules in the mixture 87.

The remaining molecules of the mixture 87 may then be exposed to a more effective solvent of data point 76b to dissolve larger macromolecules 88b. Again, these molecules may be decanted and the remaining mixture 87 exposed to the solvent of data point 76c to extract the largest macromolecules 88c. Each of the decanted solutions now contains a sorted set of macromolecules. The present invention has been used to identify solvents having substantially increased solvent qualities for carbon nanotubes. The same technique and similar solvents have proven to work in the exfoliation of graphene sheets from bulk graphite.

2. Liquid Phase Macromolecule Separation and Purification

The ability to form a high solute concentration thermodynamic solution of pristine macromolecules may permit macromolecules, for example carbon nanotubes or graphene sheets, to be sorted by some physical property of the macromolecule, such as size. Such sorting processes use, for example, chromatography, electrophoresis, dielectrophoresis, density gradient centrifugation, filtration, fractional precipitation, or solventization.

With the accurate characterization of the solvent quality of multiple solvents for a given solute, as provided by the data of the graph in FIG. 3, it is possible not only to identify an improved solvent, but also to create improved separation of mixed solutes, for example, mixtures of graphene sheets of different sizes. This separation may use the different solvents (including varying ratios of two solvents having different solvent qualities) to selectively dissolve macromolecules of different sizes taking advantage of a slight dependency between molecule size and solubility of the molecule. Alternatively, a solution of a mixture of molecules may have the quality of its solvent altered by mixing it with another solvent to selectively precipitate molecules from solution.

More particularly, the ability of these solvents to form solutions of graphene is also believed to enable the solutions to exfoliate individual sheets of graphene from bulk graphene positioned within an amount of the solvent. This can be accomplished by placing an amount of bulk graphene within an amount of a solvent having a surface tension value of between about 38.4 mJ/m$^2$ and about 40.4 mJ/m$^2$, a value of chi less than about 0.01 or a dispersion limit of graphene within the solvent of greater than about 0.05 mg/ml. After placing the graphite within the solvent, the solvent will act on the graphite to exfoliate individual sheets of graphene from the bulk graphite. The size of the sheets of graphene that are exfoliated can be controlled through the selection of the particular solvent used, as solvents having surface tension values closer to the optimal value will be able to exfoliate larger sheets, while solvents having surface tension values to either side of the optimal value will be less effective at solvating the graphite, resulting in the exfoliation of smaller graphene sheets.

For example, as shown in FIG. 4, a mixture 87 of nano-structure molecules such as nanotubes, aggregated sheets of graphene or a block of graphite having sheets of graphene thereon, may be exposed to the first solvent of data point 76a to promote the dissolution of small macromolecules 88a, the solvent of data point 76a providing less solubility of larger macromolecules. Once in solution, these smaller macromolecules may be decanted together with the solvent and thereby isolated from the other molecules in the mixture 87.

The remaining molecules of the mixture 87 may then be exposed to a more effective solvent of data point 76b to dissolve larger macromolecules 88b. Again, these molecules may be decanted and the remaining mixture 87 exposed to the solvent of data point 76c to extract the largest macromolecules 88c. Each of the decanted solutions now contains a sorted set of macromolecules.

Examples of other sorting techniques using dispersions are described in the following publications, U.S. patents and patent applications hereby incorporated by reference, such as may form a basis for use of the present invention.

United States Patent Application 20050067349, Directed Flow Method And System For Bulk Separation Of Single-Walled Tubular Fullerenes Based On Helicity, describes a method for bulk separation of single-walled tubular fullerenes by helicity using a solution or suspension of the single-walled tubular fullerenes flowed onto a crystalline or highly oriented substrate.

United States Patent Application 20070009909, Sorting Of Carbon Nanotubes Through Arrays, describes sorting metallic and semiconducting CNTs of differing lengths and diameters by flowing them through an arrangement of fixed structures such as an array of posts or studs.

One method of separating metallic from semi-conducting SWNTs in a suspension using alternating current dielectrophoresis is reported by Krupke, et al, Science, 301, 344-347 (2003).

United States Patent Application 20040038251, Single-Wall Carbon Nanotubes Of Precisely Defined Type And Use Thereof, describes centrifugation to separate single-wall nanotubes from other materials.

United States Patent Application 20060231399, Single-Wall Carbon Nanotube Compositions, describes a nanotube suspension acidified to protonate a fraction of the nanotubes. An electric field is applied and the protonated nanotubes migrate in the electric fields at different rates dependent on their (n, m) type.

In addition to carbon nanotubes, including SWNT and MWNT, the present invention may work for sorting other carbon macromolecules such as fullerenes or "buckyballs".

3. Liquid Phase Macromolecules Manipulation and Assembly

The ability to form a high concentration thermodynamic solution of pristine macromolecules, for example, graphene sheets, is expected to facilitate liquid phase manipulation and assembly techniques. Such manipulation and assembly techniques may include alignment or manipulation of the graphene macromolecules in suspension by means of fluid flow, electrical fields (as in electrophoretic deposition), spraying, painting, atomization, or printing processes. Such manipulation and assembly techniques may further include dispersion prior to incorporation in a solid matrix or evaporative surface coating.

Examples of these techniques employed using other dispersions are described in the following publications hereby incorporated by reference such as may form a basis for use of the present invention.

Q. Chen et al., (Applied Physics Letters (2001), 78, 3714) describes using electrical fields while filtering dispersions of SWNTs to form thick films of aligned nanotubes.

Sallem G. Rao et al., (Nature (2003), 425, 36) describes using chemically functionalized patterns on a substrate to align sonicated SWNTs.

Yu Huang et al., (Science, Vol. 291, pg 630-633) describes forming aligned nanostructures by passing suspensions of nanowires through fluidic channels between a substrate and a mold.

R. Smalley et al. (WO0130694) describes aligning of nanotube ropes in the presence of a 25 Tesla magnetic field.

Patent Application 20040228961, Controlled Deposition And Alignment Of Carbon Nanotubes, describes using electric fields to align the carbon nanotubes which may then be adhered to a surface treated with an "attraction material."

4. Liquid Phase Chemical Processing

The ability to form a high concentration thermodynamic solution of pristine macromolecules, for example, graphene sheets, is expected to permit improved chemical processing of the macromolecules, for example functionalization, absorption, adsorption and entrainment of other chemicals, coatings with other chemicals, etching, oxidation and the like.

Examples of these techniques employed using other dispersions are described in the following patent hereby incorporated by reference such as may form a basis for use of the present invention.

United States Patent Application 20080063587, Functionalization Of Carbon Nanotubes, describes suspending carbon nanotubes in a solvent to react preferentially with a functionalizing species based on the electronic properties of the carbon nanotubes, and then sorting the carbon nanotubes by selective functionalization and electrophoresis.

5. Surface Coatings

As will be described, the present invention has been used to determine high-quality solvents for carbon nanotubes and graphene. Once in solution these carbon materials may be more evenly applied to a surface, the solvent acting as a carrier for spraying or printing and providing improved separation of the molecules. After distribution of the molecules on the surface, the solvent may be removed, for example by evaporation, or hardened, for example, by polymerization or other techniques to hold the dissolved macromolecules in their dispersed state on the substrate.

In the case of a graphene solution, a solvent may remain in liquid form and be used simply as a carrier to introduce the graphene into the areas requiring lubrication. Or the solvent of the graphene may be removed and used simply to deposit a uniform film of graphene on the substrate. If the film is applied to a metal or other surface acquiring carbon treatment, a layer of graphene may be heated so that the substrate absorbs the carbon in a uniform manner. A thin uniform layer of graphene may be annealed to promote interconnection between graphene molecules providing for a continuous electrically conductive surface. This heating may be accompanied by the introduction of carbon in an environment normally used for the growing of graphene to speed a graphene growth process.

6. Transparent Electrodes

Figure 18:
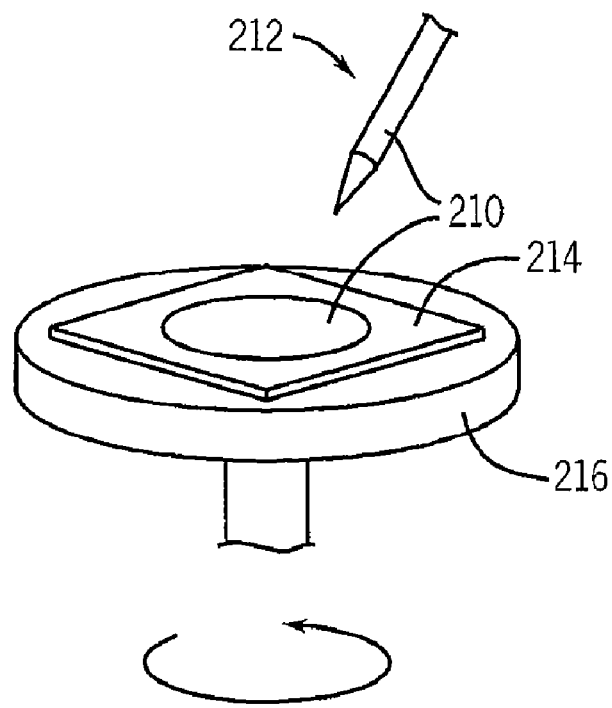
FIG. 18 is a schematic representation of an apparatus for spin coating solventized graphene onto a substrate.

Referring to FIG. 18, a solution 210 containing graphene in thermodynamic equilibrium with a solvent, for example, a mixture of CHP and NMP solvents, has been deposited by pipette 212 on a substrate, for example, including a silicon wafer and a glass plate and spread in a thin layer by a spin coating process where the substrate 214 is attached to a rotating table 216. After spin coating, the substrate 214 was heated in an oven to expel the solvents or vacuum dried and this process repeated with additional layers deposited by spin coating on top of the first layer and the substrate again baked or dried.

Example IV

Spin-Coated Graphene Sheets from Equilibrium Solution Onto Silicon Wafers

Thin graphene films were deposited onto silicon and glass substrates by spin-coating thin layers of a liquid solution of graphene thermodynamically dissolved in the solvent N-cyclohexyl-2-pyrrolidone (CHP) onto Si wafers and glass microscope slides having areas greater than 1 $cm^2$. Any of the other solvents or solvents having the ranges described herein for graphene may also be used.

It is believed that this solution contains many graphene sheets comprising monolayer, bilayer, and multilayers of graphene. Studies have established that as many as 30% of the graphene sheets are one atomic layer thick using these solvents. As used herein, graphene sheet means single or multilayer graphene with a nanoscale thickness (<1000 nm). It is believed that this solvent permits the creation of a solution consisting of about 30% single monolayer graphene and thus greater than 10% single monolayers and that the solution consists of greater than 10% graphene sheets of less than three monolayers. The layer formed is discrete, meaning not part of a larger graphite body but either free standing or attached to a dissimilar substrate.

The solvent molecules of the solution on the substrate are then evaporated by heating the system. Specifically, small amounts of graphene solution (less than 0.1 mL) were pipetted onto Si wafers/glass slides, which were then spun at 3000 rpm for approximately 10 seconds (accelerated to 3000 rpm at 1000 rpm/sec.). After spinning the graphene solution onto the wafer/slide to create a very thin coating, the Si wafer/slide was placed directly on a 250° C. hot plate to evaporate the CHP. Then the process of pipetting, spinning, and heating were repeated up to 50 times to deposit additional layers of graphene to eventually form a conductive, yet transparent graphene film. Samples of graphene deposited onto Si wafers were also heated for several hours in a 700° C. furnace. Transparent in this context means subjectively transparent at visible light frequencies to a human observer.

Figure 27:
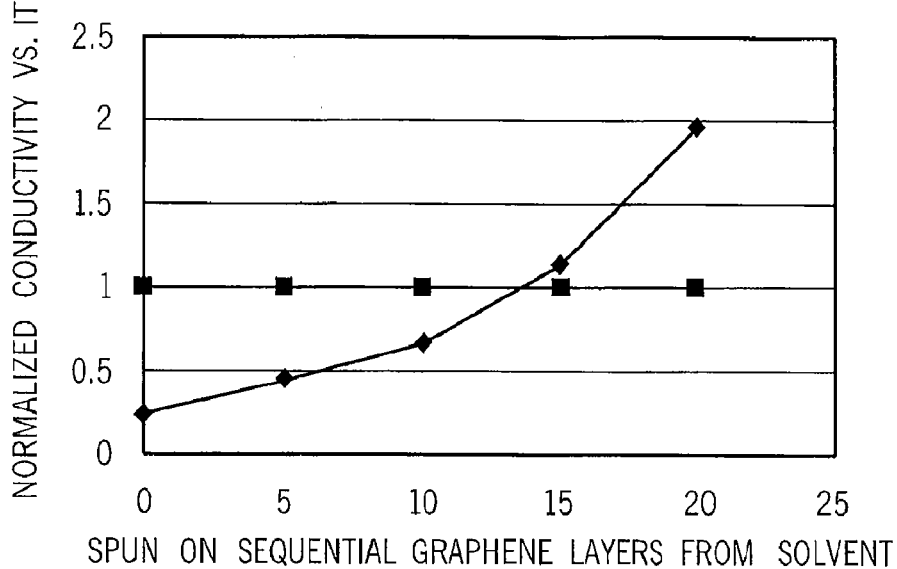
FIG. 27 is a graph showing surface conductivity versus sequential depositions of graphene plotted against surface conductivity of a standard indium tin oxide coating.
Figure 28:
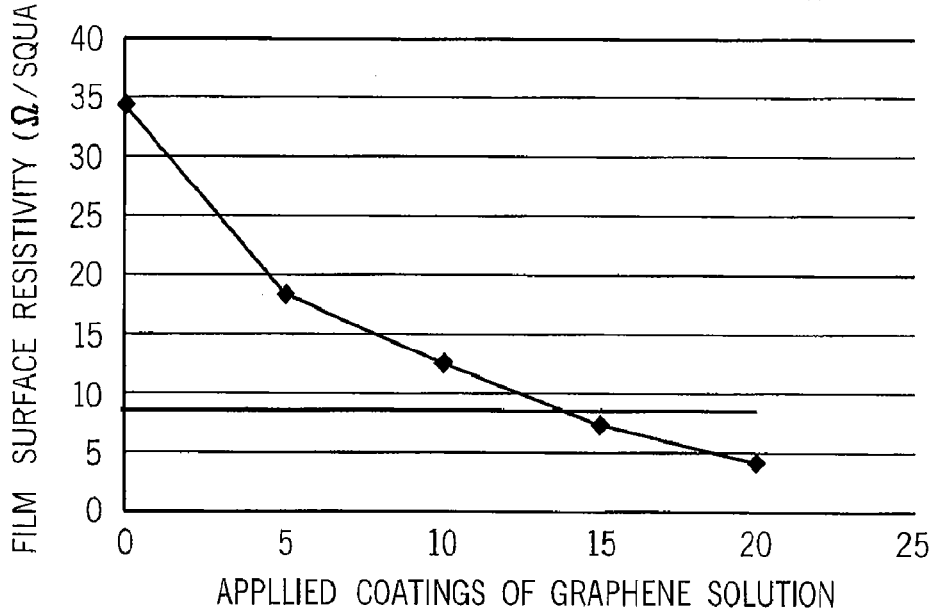
FIG. 28 is a figure similar to that of FIG. 27 showing resistance.

The conductivity of the surface of a silicon wafer is shown in FIGS. 27 and 28 with the conductivity of the graphing film exceeding that of commercial indium tin oxide (ITO) at approximately 15 application/annealing cycles. This layer is only a few nanometers thick, greater than 1 $cm^2$ in area and far less than the 10 μm thickness of commercial ITO. The conductivity of FIG. 27 is normalized to that of ITO.

TABLE VII

The effect of furnace treatment on film conductivity:

| Sample | Resistance |
| --- | --- |
| Furnace-treated graphene-coated Si (20 coatings applied) | 4.32 Ω/square |
| Graphene-coated Si (20 coatings) without furnace treatment | 12.4 Ω/square |
| ITO-coated glass slide (control) | 8.48 Ω/square |

These data show the conductivity of a graphene film deposited onto a silicon wafer from solution. It is believed that heating the deposited graphene film, in this case in a furnace, is helpful to improving its conductivity, perhaps through the annealing of adjacent non-covalently linked graphene sheets on the substrate surface.

Figure 19:
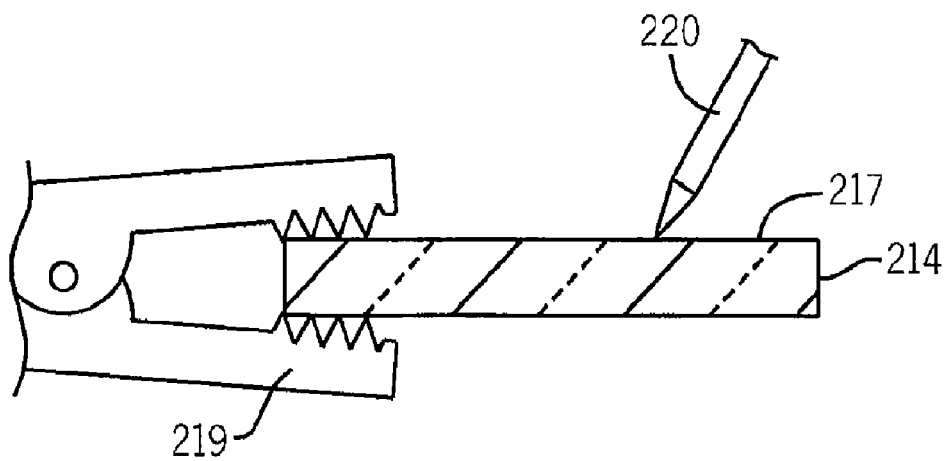
FIG. 19 is a cross-section of the substrate of FIG. 18 showing an experimentally verified connection to the graphene sheet using a plated steel alligator clip.

Referring to FIG. 19, a thin graphene film 217 after 15 repetitions of this process provides a sheet resistance, measured using a four terminal technique, lower than that for a 210μ layer of ITO. Direct electrical contact to the graphene film may be made with an alligator clip 219 or conductive probe 221 apparently without an intervening gold contact over plating and the layer appears to be much thinner than ten microns.

Example V

Spin-Coated Graphene Sheets from Equilibrium Solution Onto Glass Slides

TABLE VIII

Graphene deposited on glass:

| Sample | Resistance |
| --- | --- |
| Glass slide coated with 30 successive applications of graphene solution (heated on 250° C. hot plate after each application to evaporate solvent) | 6.89 Ω/square |
| Glass slide without any coating | 146 kΩ/square |
| Glass slide coated with one single application of graphene solution (applied solution volume equivalent to 30 separate applications above) | 87 kΩ/square |
| ITO-coated glass slide (control) | 8.48 Ω/square |

These data provide the first demonstration of a discrete conductive graphene film deposited from dissolved graphene in solution. In this context, a discrete film means that the film is not the upper surface of bulk of graphite but is in a layer isolated from other graphene. This film covers a large area (over 5 cm$^2$), is optically transparent, and has a surface conductivity greater than indium tin oxide (ITO) a material currently used as a transparent electrode in applications such as LCD's and solar cells. In addition, the above table shows that applying and evaporating many thin coatings of graphene solution to the glass slide successively leads to a highly conductive film, while applying a single, thick solution coating to a glass surface and evaporating all the CHP solvent at once leads to a film that is less conductive.

It is expected that this process may employ a substrate that is pretreated, for example, by heating the substrate in the presence of oxygen to oxidize the surface, and the graphene layer at the conclusion of the coating process or at points between individual coatings may be heated in the presence of oxygen or in a reducing atmosphere of hydrogen, methane, or carbon monoxide to promote joining of the graphene platelets. Alternatively the heating may be conducted in a relatively inert atmosphere of argon, nitrogen, or helium. Freeze drying may be a preferred method of solvent removal. It is contemplated that the coating process may be performed in a large process chamber in which large substrates are repeatedly liquid coated and then the films freeze dried or dried by another method such a heating, laser treatment/evaporation, centrifugal evaporation or vacuum desiccation.

These latter drying techniques would permit coating plastics, for example, to produce antistatic polyethylene bags or the like.

The resulting coating can be used as an electrode, for example on the touchscreen or as a cathode for an LCD display or plasma television panel. Alternatively, an electrode coated with individual particles of graphene may be bombarded with high-energy electrons or the like in a sputtering process to distribute graphene over a surface. The above approaches may also be used in the other examples where films of graphene are required.

Example VI

Self-Assembled Graphene Film

Figure 20:
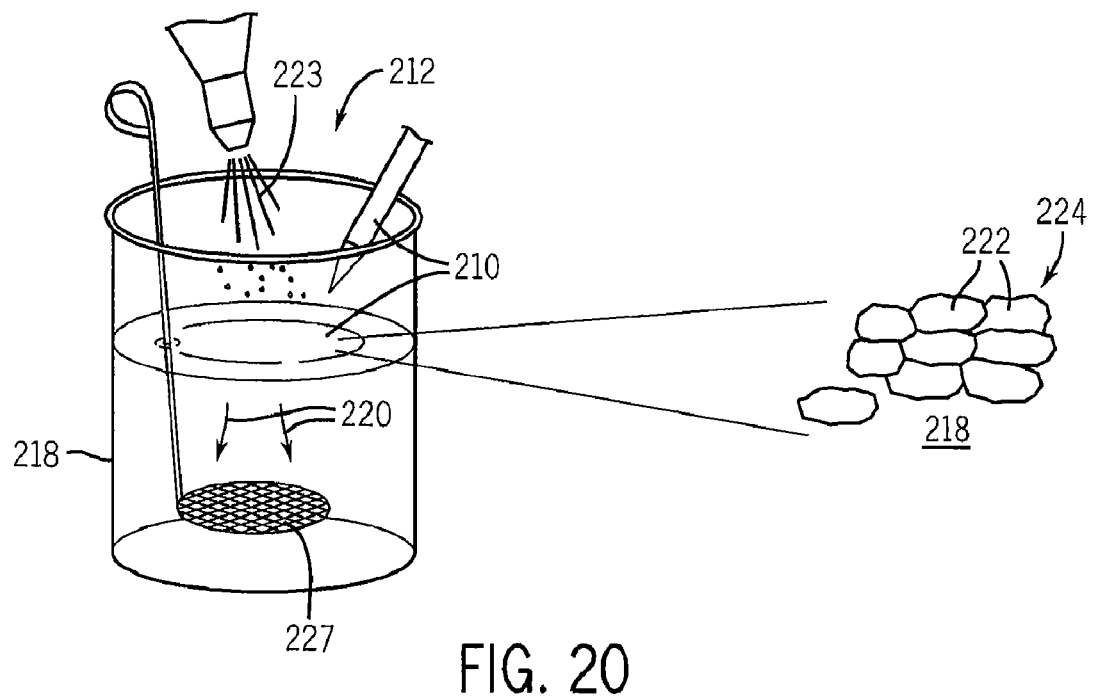
FIG. 20 is a schematic representation of an experimental assembly of graphene sheets at a water air interface in a beaker showing a possible mechanism of self-assembly.

Referring to FIG. 20, the solution 210 described above may alternatively be deposited on the surface of water 218 and the water may draw into it the solvents 220 of the solution leaving on its surface platelets 222 of graphene which then self-assemble in edgewise fashion as a result of surface energy affects. Alternatively, the solution 210 may be mixed with the water to yield a temporary emulsion which rises to the water surface for self-assembly of the platelets 222. Large area interconduction between the platelets 222 is suggested by the formation of a highly reflective surface spanning many square millimeters of area indicating high electron mobility. This reflectivity is observed at an angle of incidence normal to the surface for visible light by a human observer. A graphene skin 224 formed by the self assembled platelets 222 may be locked in place by the addition of a polymer 223, for examples, sprayed on top of the platelets 222 or by other means including lifting the skin 224 from below using perforated material 227 having holes smaller than the graphene sheets, for example, a transmission electron microscope grid or by floating the skin 224 upon a substrate to be dried there. Subsequent transfer of the skin 224 to another surface may also be performed and the skin 224 heated as described above to fuse the graphene platelets into a continuous monolayer.

It may be possible to treat the edges of the graphene sheets to promote their interconnection, for example at the interface between liquid boundaries or on a substrate into a single sheet. The edge treatment may then be removed.

7. Solar Cells

Figure 21:
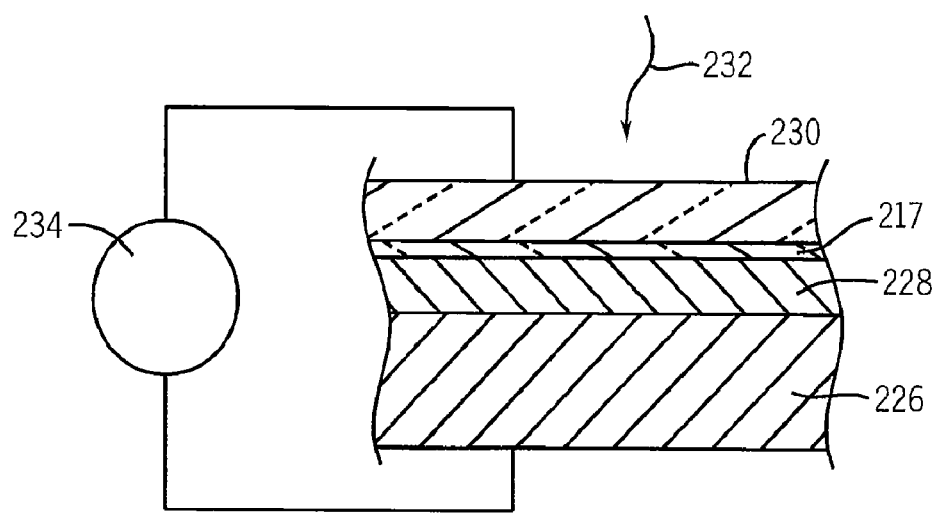
FIG. 21 is a cross-section through a solar cell constructed using a transparent graphene electrode fabricated as shown in FIG. 18.

Referring to FIG. 21, a solar cell has been produced using the solution 210 described above by applying a graphene layer 217 to a backside of a glass cover plate 230 allowing the passage of light 232 therethrough to a photoactive layer 228. The photoactive layer 228 may be supported on a conventional conductive substrate 226, for example a silicon wafer, and power may be extracted by a device 234, for example a voltmeter or other load.

8. Composites

Polymerization or solidification of the solvent can also be used directly on the solution to provide for three-dimensional composite materials having a more uniform distribution of carbon structures for strength or improved conductive properties in that composite material. Conductive composite materials having a relatively high resistance may be used for protection against static electricity and electrical shielding. Conductive composite materials having relatively low resistance may be used for printed wiring and the like. Carbon nanotubes and/or graphene can be mixed into a polymer and then the solvent evaporated to provide the above properties of improve strained and or increased conductivity. Sheets of graphene can be mixed into a polymer and then the solvent evaporated to provide the above properties of improve strained and or increased conductivity. Likely polymer candidates for graphene and carbon nanotubes that take advantage of include but are not limited to nitrogen and or hydrogen bond containing polymers such as polyurethanes, polypyrrolidones, polyvinyl alcohols, polyimides, polyamides, polysaccharides, nylons and proteins, DNA and epoxies.

Example VI

Conductive Polymers

Conductive/decreased resistance films were made by dissolving polyurethane, kaptons (polyimides), polypyrrolidones and PMMA polymers in CHP and other pyrrolidone solvents then blending with CHP and graphene and casting thick films onto glass slides. The films, when peeled from glass they were cast on, did not deflect the electrostatic meter and are hence at least electrostatic dissipative and, at most, conductive. Many films showed increased strength and conductivity with graphene.

Freeze drying may be used for solvent removal from both the thin films or another method such as heating, laser treatment/evaporation, centrifugal evaporation or vacuum desiccation may be used.

The above examples describe the use of graphene but should also be considered to include combinations of graphene and other nano carbon particles such as carbon nanotubes. In particular, the solvents discovered by the present inventors can simultaneously dissolve graphene and carbon nanotubes, for example, allowing thermodynamic mixing of the two for high degrees of homogeneity. In one example, a solvent may be optimized for the material that is less easily dissolved (for example, graphene) which nevertheless overlaps as a solvent for the other material that is more readily dissolved (for example, carbon nanotubes). Alternatively, a solvent may be optimized for the combination. In addition, one or more of the carbon allotropes may be functionalized to shift its solvent "resonance" to match that of the other carbon allotropes.

It is believed that the present invention, by providing a potential source of low-cost graphene will enable a wide variety of additional products and processes in which graphene replaces more expensive carbon nanotubes and other carbon allotropes.

9. Ink

A conductive ink or paint may be fabricated using nanographene or graphene sheets and a solvent, as is described in co-pending applications by the same inventors, optionally including an organic binder. The ink may be printed or otherwise dispensed on the substrate and the solvent allowed to evaporate, possibly with the application of heat or in the presence of a vacuum. The ink may be used to form printed wiring or for other conductive applications, for example electromagnetic interference shielding. Alternatively, the ink or paint may be used simply to provide a surface protection offering a chemically resistant and mechanically strong protective layer.

10. Supercapacitors

Graphene sheets may be utilized to construct an electrochemical capacitor or super capacitor. In this case, the graphene sheets may be used in lieu of carbon nanotubes or other carbon allotropes as is taught in the prior art. In such applications, the graphene provides a matrix having extremely high surface area that may be coated with a dielectric layer or left in a pristine state and separated by graphene coated with an insulating layer.

It is expected that graphene will exhibit anomalous polarizability which could present valuable optical or electrical properties, for example in the former case as a dielectric material.

11. Flame Retardant Materials

A fire or flame retardant material may be constructed using graphene sheets whose high rate of thermal conductivity helps reduce surface temperatures of the material to those below that necessary to support combustion. Such materials may be prepared, for example, by dispersing graphene sheets in a solvent and then introducing the solvent into a polymer matrix. The solvent may then be extracted. Alternatively the solvent itself may be polymerized. In this case, individual graphene sheets are not required so long as the number of laminations of graphene in each element is limited so as not to adversely affect the strength or property of the composite material as might be the case with bulk graphite. The polymer matrix may also have solvent properties to promote separation of the graphene. The graphene in a matrix may then be incorporated into another material, for example a thermoplastic material, or may be molded itself.

12. Fuel Cells

It is believed that a fuel cell may be constructed using graphene sheets as a replacement for carbon nanotubes, fullerenes, etc. as are now proposed.

13. Batteries

Graphene sheets may be used similarly to create or enhance the electrodes for a battery structure, again, relying on the conductive property of extremely low resistance and the ability to provide a very high surface area. Typically, the graphene sheets have less electrical resistance than an electrically conductive polymer. Moreover, the presence of the graphene sheets serves as a filler, increasing mechanical strength of the matrix. Graphene may also be used for the construction of solar cells as an electrode, light pipe, or as a basis for deposition of other materials such as zinc and tin oxide.

14. Lubricants

It is believed that a lubricant may be compounded utilizing graphene sheets that are not fully separated from each other, for example in sheets of ten to a hundred, as effected by controlling the solvent properties as affects the thermodynamic equilibrium of graphene sheets in an individual low entropy state and collected together in a higher entropy state.

The graphene sheets provide for a more finely dispersed lubricant than can be obtained with even the most finely powdered graphite. Further, the lubricant may include the solvent to promote a separation of the graphene sheets for a more uniform dispersion and particularly, enhanced penetration of sealed or recessed surfaces. It is possible that graphene can be used in a lubricant composed according to the techniques described in U.S. Patent Publication Nos. 20020095860 and 20010041663 substituting graphene sheets for carbon nanotubes. While the inventors do not wish to be bound to a particular theory, lubrication may be provided by a mutual slipping of graphene particles, or by the surface coated graphene serving as a lubricating layer in the presence of atmospheric moisture.

15. Fuel Additives

It is believed that graphene may be used to create a fuel additive to be combined with other hydrocarbon fuels and oils. The graphene sheets may provide carriers for fuel additives, may contribute to anti-knock properties for the fuel and lubrication of the engine, and may increase the energy density of the fuel.

16. Catalytic Surfaces

Graphene sheets may provide a matrix for the construction of catalysts or serve as catalysts in their own right. Again the high surface area of a graphene matrix may be enlisted to improve the reactive surface of the catalyst.

17. Activated Carbon Filters

Similarly, graphene may provide a basis for activated carbon filters by solvent generation of the graphene sheets and recombination of the graphene sheets into a high surface area matrix.

18. Automotive Tires

Graphene sheets may be added to materials to improve their electrical or thermal conductivity and, in particular, may be added to elastomers for that purpose. A particular example is the production of tires incorporating graphene to provide improved dispersion of heat that can otherwise limit the life of the tire.

19. Flow Sensors

Graphene sheets may be used to construct a novel flow sensor for measuring liquid flow velocities along a direction of liquid flow by introducing graphene sheets into the liquid arranged between two conducting elements. The two conducting elements are adapted to measure changes in resistance or electricity generated by the graphene sheets in a magnetic field as a function of the rate of flow of the liquid.

20. Drug Carriers and Contrast Media

Graphene sheets may find use as carriers for drugs that may be introduced into the body or as contrast media for medical imaging systems. The pristine carbon of the graphene should be biocompatible and the surface of the graphene can be functionalized, for example when in solution, to provide for attachment to drug molecules.

21. Taggants

Graphene sheets sorted by size, for example, may be used as a taggant to identify materials or as a tracker.

22. Sunscreen

Figure 31:
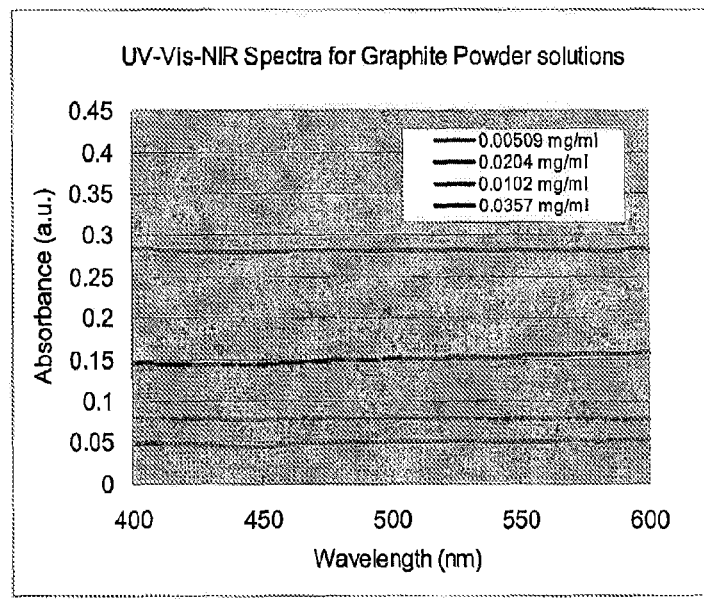
FIG. 31 is a graph showing changes in absorbance with light frequency for a visible light range.
Figure 32:
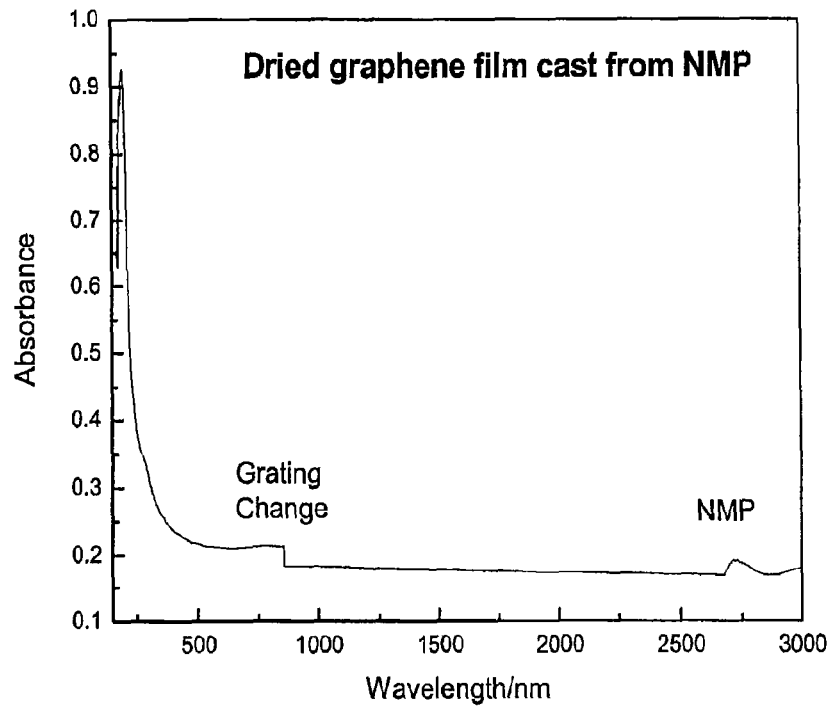
FIG. 32 is a graph showing absorbance of a graphene layer as a function of light frequency in the ultraviolet region and visible region on a glass slide.
Figure 33:
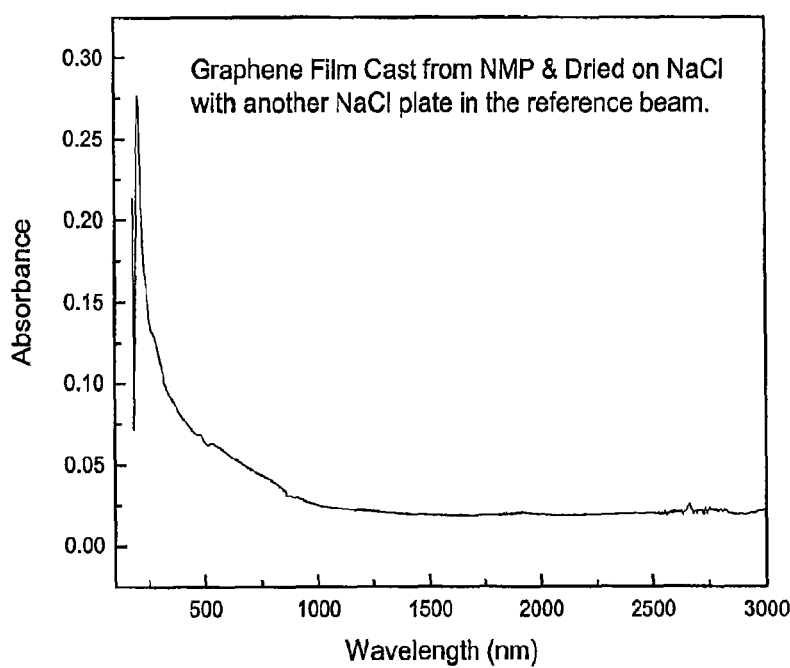
FIG. 33 is a graph similar to that of FIG. 32 with the graphene layer supported on NaCl.

Graphene sheets may be incorporated into topically applied solutions to provide an ultraviolet sunblock. Referring to FIGS. 31-33, graphene provides significant attenuation of ultraviolet light while being substantially clear to visible light frequencies. A sunscreen can be prepared by creating a solution of graphene further present invention and mixing it with natural or synthetic oils, including for example, cocoa butter or the like or carrier fluids such as PEG-6. The solvent may then be extracted, for example by evaporation, preserving the graphene in a colloid or viscous suspension to be applied as a sunscreen to the skin. Alternatively the graphene may be incorporated into matrix materials such as thin plastic films to provide ultraviolet resistance to degradation of the underlying polymer.

23. Thermodynamically Stable Composite Materials

Graphene sheets may be incorporated into polymer materials to form composite materials to change the electrical or mechanical properties of those materials. Several techniques may be used for such synthesis. First, the graphene and or carbon nanotubes may be dissolved in a polymer or monomer that provides a good thermodynamic solvent for the graphene or carbon nanotubes. Polyurethane appears to be a good solvent polymer. The graphene or carbon nanotubes may be mixed with a less viscous solvent (for example NMP, CHP) and then added as a solution to the polymer, the former solvent which may then be evaporated out of the polymer which remains holding the graphene or carbon nanotubes in thermodynamic suspension. Alternatively, the graphene or carbon nanotubes may be incorporated into liquefied polymer directly, for example, prior to cooling (for thermoplastics).

In the case of the monomer, after the graphene or carbon nanotubes are dispersed in a low viscosity monomer (or via the solvent route described above), the monomer may be cured to polymerized the monomer. This approach may use any of a range of condensation polymers.

Alternatively, or in addition, graphene may be functionalized with materials such as isocyanate, carboxyl acids, hydroxyls, amines, and amides while the graphene is suspended in a solvent. The functionalizing materials may then form covalent bonds with a polymer or monomer when a solventized graphene is mixed with the polymer or monomer, there after allowing evaporation of the solvent to occur without clumping of the graphene which is stabilized by the functionalization.

Alternatively, the graphene may be functionalized for example with C18 acids to shift the characteristics of its solvent, for example from NMP to chloroform as determined by the instrument created by the present inventors. This substitute solvent may then be used to dissolve common polymers such as polystyrene allowing the graphene to be dispersed in the solvent in the polystyrene and then evaporated therefrom.

24. Functionalized Graphene

In solution, the graphene is readily functionalized for many other purposes. The graphene may be functionalized for example with catalysts using an autocatalytic deposit of a metal or of particles attached to metals. Functionalization may be used to attach the graphene to other structures such as quantum dots or photoactive compounds, for example, in photoelectric devices.

25. Cellular Scaffolds

Graphene may be used as a synthesis scaffold for building biological materials, for example at the cell level, or for other chemical synthesis problems.

It is specifically intended that the present invention not be limited to the embodiments and illustrations contained herein and the claims should be understood to include modified forms of those embodiments including portions of the embodiments and combinations of elements of different embodiments as come within the scope of the following claims. For example, other measures of solvent quality (other than $B_2$, $\chi$, and $\Delta H_{Mix}$) may be employed, including, for example, Zeta potential or aggregate size distribution evaluated using micrographs. While the invention has been tested with single walled carbon nanotubes and graphene, it is believed that the present invention may also work with other materials such as molybdenum sulfide, mica, and clay as well as biomolecules such as proteins and DNA and RNA and crystalline cellulose. Generally the instrument described herein may be suitable for measuring the characteristics of solutions of other nanoparticles, colloidal systems, and perhaps polymers. The present method may also provide a determination of the thermodynamic stability of plastics and plasticizers and polymer blends.

Generally, the present invention can be expected to improve the above processes that use graphene sheets and that normally require surfactants or dispersants and extensive mechanical agitation by either eliminating the surfactants, dispersants, and agitation or augmenting them. The ability to produce a true thermodynamic solution with a significant concentration of these materials leads to expected improvements in a variety of processes in which these solutes are dispersed in a "pristine" form, meaning without additional functionalization, surfactant or dispersion coatings. The present system can be distinguished from systems suspending macromolecules in materials identified as solvents in a general sense (that is, they serve as solvents in some contexts) because such suspensions typically do not create equilibrium thermodynamic solutions. Further, the present invention describes solvents for equilibrium thermodynamic solutions having substantially higher dispersion limits than previously believed possible.

The invention also contemplates that processes normally requiring suspensions of carbon nanotubes may permit substitution of graphene in a solvent due to the ability of these solvents to form true solutions of sheets of graphene, to take advantage of some of the enhanced properties of graphene over nanotubes.

Additionally, each of the above solvents was tested at ambient temperatures and pressures with respect to their ability to form a true solution with the graphene. It is believed that changes in the temperature and/or pressure will alter the ability of the solvents to form a solution with the particular carbon allotrope. As a result, it is also contemplated that those solvents, that at ambient temperature and pressure cannot form or only form solutions with very low concentrations of the carbon allotrope, will become effective at elevated temperatures and/or pressures.

What is claimed is:

1. A method of preparing a polymer composite comprising the steps of:
    (a) placing bulk, non-functionalized graphite in a solvent;
    (b) exfoliating graphene sheets directly from the non-functionalized graphite placed in the solvent as a result of the interaction of the non-functionalized graphite with the solvent;
    (c) dispersing the graphene sheets exfoliated directly from the bulk, non-functionalized graphite in the solvent, wherein the solvent is characterized by a value of chi less than about 0.08; and
    (d) capturing the dispersed graphene sheets in a substantially solid phase polymer matrix.

2. The method of claim 1 wherein the value of chi for the solvent is less than 0.01.

3. The method of claim 1 wherein the value of chi for the solvent is substantially between 0.00 and −0.13.

4. The method of claim 1 wherein step (b) mixes the solvent-graphene solution with the polymer and then removes the solvent.

5. The method of claim 1 wherein step (b) includes the steps of first dissolving a polymer in a polymer solvent and then mixing the polymer and polymer solvent with the graphene-solvent solution and extracting the polymer solvent.

6. The method of claim 5 wherein the step of extracting the polymer solvent includes at least one of the steps of freeze-drying, heat drying, laser treatment, centrifugal evaporation, and vacuum desiccation.

7. The method of claim 1 wherein step (b) includes the step of hardening the solvent to provide the polymer matrix.

8. The method of claim 1 wherein the solvent in step (a) is a thermoplastic heated to reduce its viscosity during step (a) and wherein step (b) consists of cooling the thermoplastic after step (a).

9. The method of claim 1 wherein a polymer of the polymer matrix is a nitrogen or hydrogen containing polymer.

10. The method of claim 9 wherein the polymer matrix is selected from the group consisting of: polyurethanes, polypyrrolidones, polyvinyl alcohols, polyimides, polyamides, polysaccharides, nylons, proteins, DNA, PMMA polymers and epoxies.

11. The method of claim 1 further including the steps of:
    (a) dispersing carbon nanotubes in a solvent-carbon nanotube solution, the carbon nanotube solution characterized by a value of chi less than about 0.08; and
    (b) incorporating the carbon nanotubes as dispersed by the solvent-carbon nanotube solution into the polymer matrix.

12. The method of claim 11 wherein the solvent of the solvent-carbon nanotube solution is different from the solvent of the solvent graphene solution.

13. The method of claim 1 wherein the graphene is pristine.

14. A method of preparing a polymer composite comprising the steps of:
    (a) dispersing graphene sheets in a solvent, the graphene sheets exfoliated directly from bulk, non-functionalized graphite that is placed in the solvent, wherein the solvent is characterized by a value of chi less than about 0.08; and
    (b) capturing the dispersed graphene in a substantially solid phase polymer matrix by hardening the solvent to provide the polymer matrix,
wherein the solvent is a monomer and hardening is a polymerization of the solvent.

15. A method of preparing a polymer composite comprising the steps of:
    (a) dispersing graphene sheets in a solvent, the graphene sheets exfoliated directly from bulk, non-functionalized graphite that is placed in the solvent, wherein the solvent is characterized by a value of chi less than about 0.08; and (b) capturing the dispersed graphene in a substantially solid phase polymer matrix, wherein step (b) mixes the graphene-solvent solution with a polymer that forms the polymer matrix, wherein the polymer is the solvent for the graphene.

16. A method of preparing a polymer composite comprising the steps of:
   (a) placing bulk, non-functionalized graphite in a solvent;
   (b) exfoliating graphene sheets directly from the non-functionalized graphite placed in the solvent as a result of the interaction of the non-functionalized graphite with the solvent;
   (c) dispersing the graphene sheets exfoliated directly from the bulk, non-functionalized graphite in the solvent, wherein the solvent is characterized by a surface tension value substantially between about 36 mJ/m$^2$ and 43 mJ/m$^2$; and
   (d) capturing the dispersed graphene sheets in a substantially solid phase polymer matrix.

17. The method of claim 16 wherein the solvent has a surface tension value substantially between about 37 mJ/m$^2$ and 42 mJ/m$^2$.

18. The method of claim 16 wherein the solvent has a surface tension value substantially between about 38.4 mJ/m$^2$ and 40.4 mJ/m$^2$.

19. The method of claim 18 wherein the solvent is a pyrrolidone.

20. The method of claim 19 wherein the solvent is selected from the group consisting of: cyclohexyl-2-pyrrolidone, N-methyl-2-pyrrolidone, N-ethyl-2-pyrrolidone and N-octyl-2-pyrrolidone, and mixtures thereof.

21. A method of preparing a polymer composite comprising the steps of:
   (a) placing a block consisting of non-functionalized graphite in a solvent;
   (b) exfoliating graphene sheets directly from the non-functionalized graphite placed in the solvent as a result of the interaction of the non-functionalized graphite with the solvent;
   (c) dispersing the graphene sheets exfoliated directly from the block consisting of non-functionalized graphite in the solvent, wherein the solvent is selected from the group consisting of: N-methyl-2-pyrrolidone, cyclohexyl-2-pyrrolidone and mixtures thereof; and
   (d) capturing the dispersed graphene in a substantially solid phase polymer matrix.

* * * * *